United States Patent
Deno et al.

(10) Patent No.: US 6,738,667 B2
(45) Date of Patent: May 18, 2004

(54) IMPLANTABLE MEDICAL DEVICE FOR TREATING CARDIAC MECHANICAL DYSFUNCTION BY ELECTRICAL STIMULATION

(75) Inventors: D. Curtis Deno, Andover, MN (US); Lawrence J. Mulligan, Andover, MN (US); Tom D. Bennett, Shoreview, MN (US); David A. Igel, Lino Lakes, MN (US); Michael R. S. Hill, Minneapolis, MN (US); Richard J. Shaw, St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 09/750,631

(22) Filed: Dec. 28, 2000

(65) Prior Publication Data

US 2003/0074029 A1 Apr. 17, 2003

(51) Int. Cl.⁷ .............................................. A61N 1/18
(52) U.S. Cl. ............................................................ 607/23
(58) Field of Search ............................. 607/23, 18, 17, 607/9

(56) References Cited

U.S. PATENT DOCUMENTS

| | | | |
|---|---|---|---|
| 3,857,399 A | 12/1974 | Zacouto | |
| 3,939,844 A | 2/1976 | Pequignot | |
| 4,541,417 A | 9/1985 | Krikorian | 128/1 D |
| 4,554,922 A | 11/1985 | Prystowsky et al. | 128/419 PG |
| 4,674,518 A | 6/1987 | Salo | 128/695 |

(List continued on next page.)

FOREIGN PATENT DOCUMENTS

| | | | |
|---|---|---|---|
| FR | 2790967 | 10/2000 | A61N/1/368 |
| WO | WO 97/25098 | 7/1997 | A61N/1/00 |
| WO | WO 98/02209 | 1/1998 | A61N/1/375 |
| WO | WO 00/04947 | 3/2000 | |

OTHER PUBLICATIONS

Cooper, M., "Postextrasystolic Potentiation: Do We Really Know What It Means and How to Use It?," *Circulation*, vol. 88, No. 6, p. 2962–2971 (Dec. 1993).

(List continued on next page.)

*Primary Examiner*—Mark Bockelman
(74) *Attorney, Agent, or Firm*—Girma Wolde-Michael; Michael C. Soldner; Paul H. McDowall

(57) ABSTRACT

An implantable stimulator and monitor measures a group of heart failure parameters indicative of the state of heart failure employing EGM signals, measures of blood pressure including absolute pressure P, developed pressure (DP=systolic P–diastolic P), and/or dP/dt, and measures of heart chamber volume (V) over one or more cardiac cycles. These parameters include: (1) relaxation or contraction time constant tau ($\tau$); (2) mechanical restitution (MR), i.e., the mechanical response of a heart chamber to premature stimuli applied to the heart chamber; (3) recirculation fraction (RF), i.e., the rate of decay of PESP effects over a series of heart cycles; and (4) end systolic elastance ($E_{ES}$), i.e., the ratios of end systolic blood pressure P to volume V. These heart failure parameters are determined periodically regardless of patient posture and activity level. The physician can determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Drug therapies and electrical stimulation therapies, including PESP stimulation, and pacing therapies including single chamber, dual chamber and multi-chamber (bi-atrial and/or bi-ventricular) pacing can be delivered. In patient's prone to malignant tachyarrhythmias, the assessment of heart failure state can be taken into account in setting parameters of detection or classification of tachyarrhythmias and the therapies that are delivered.

8 Claims, 21 Drawing Sheets

U.S. PATENT DOCUMENTS

| | | | |
|---|---|---|---|
| 5,024,222 A | 6/1991 | Thacker | 128/419 PG |
| 5,213,098 A | 5/1993 | Bennett et al. | 128/419 PG |
| 5,328,442 A | 7/1994 | Levine | 600/17 |
| 5,331,966 A | 7/1994 | Bennett et al. | 128/696 |
| 5,417,717 A | 5/1995 | Salo et al. | 607/18 |
| 5,564,434 A | 10/1996 | Halperin et al. | 128/748 |
| 5,626,623 A | 5/1997 | Kieval et al. | 607/23 |
| 5,800,464 A | 9/1998 | Kieval | 607/9 |
| 6,021,345 A | 2/2000 | Karagueuzian et al. | 600/518 |
| 6,090,047 A | 7/2000 | Kass et al. | 600/485 |
| 6,104,949 A | 8/2000 | Pitts Crick et al. | 600/547 |
| 6,141,586 A | 10/2000 | Mower | 607/9 |

OTHER PUBLICATIONS

Dell'Italia, Louis, "Mechanism of Postextrasystolic Potentiation in the Right Ventricle," *Amer. Jour. Of Cardiol.*, vol. 65, p. 736–741 (Mar. 15, 1990).

Franz et al., "Electrical and Mechanical Restitution of the Human Heart at Different Rates of Stimulation," *Circulation Research*, vol. 53, No. 6, p. 815–822 (Dec. 1983).

Freeman et al., "Evaluation of Left Ventricular Mechanical Restitution in Closed–chest Dogs Based on Single–Beat Elastance," *Circulation Research*, vol. 67, No. 6, p. 1437–1445 (Dec. 1990).

Geschwind et al., "Sympathetic Nervous System Activation in Postextrasystolic Potentiation: Role of Catecholamine Release in Enhancement of Ventricular Function," *JACC*, vol. 4, No. 2, p. 215–225 (Aug. 1984).

Juggi et al., "Intracellular Kinetics of the Activator Calcium of Rat Heart after Ischemic Arrest and Cardioplegia: Quantitative Comparison of Right and Left Ventricles," *Can. J. Cardiol.*, vol. 8, No. 4, p. 387–395 (May 1992).

Kuijer et al., "Post–Extrasystolic Potentiation Without a Compensatory Pause in Normal and Diseased Hearts," Abstract (accepted for publication Dec. 20, 1989).

Mesaeli et al., "Mechanical Restitution and Post Extrasystolic Potentiation of Perfused Rat Heart: Quantitative Comparison of Normal Right and Left Ventricular Responses," *Can. J. Cardiol.*, vol. 8, No. 2, p. 164–172 (Mar. 1992).

Pidgeon, et al., "The Relationship Between the Strength of the Human Heart Beat and the Interval Between Beats," *Circulation*, vol. 65, No. 7, p. 1404–1410 (Jun. 1982).

Prabhu et al., "Effect of Tachycardia Heart Failure on the Restitution of Left Ventricular Function in Closed–Chest Dogs," *Circulation*, vol. 91, No. 1, p. 177–185 (Jan. 1, 1995).

Prabhu et al., "Kinetics of Restitution of Left Ventricular Relaxation," *Circulation Research*, vol. 70, No. 1, p. 29–38 (Jan. 1992).

ter Keurs et al., "Characterization of Decay of Frequency Induced Potentiation and Post–Extrasystolic Potentiation," *Cardiovascular Research*, vol. 24, p. 903–910 (1990).

van der Werf et al., "Postextrasystolic Potentiation in Man," *European Journal of Cardiology*, vol. 4/supplement, p. 131–141 (1976).

Wisenbaugh et al., "Mechanics of Postextrasystolic Potentiation in Normal Subjects and Patients With Valvular Heart Disease," *Circulation*, vol. 74, No. 1, p. 10–20 (Jul. 1986).

FIG. 4B
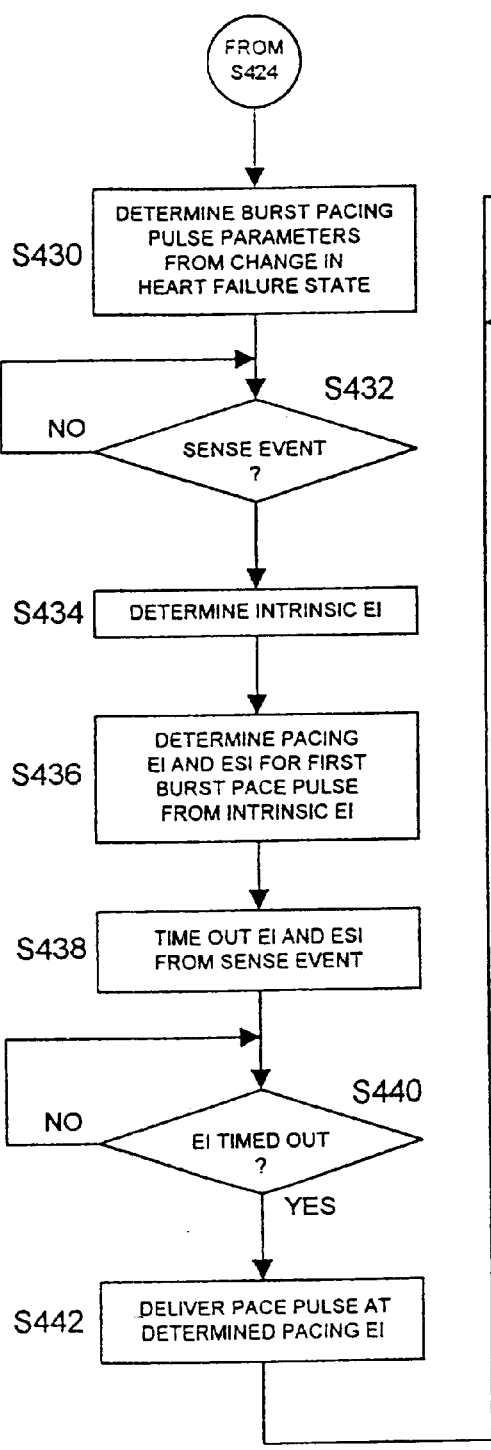
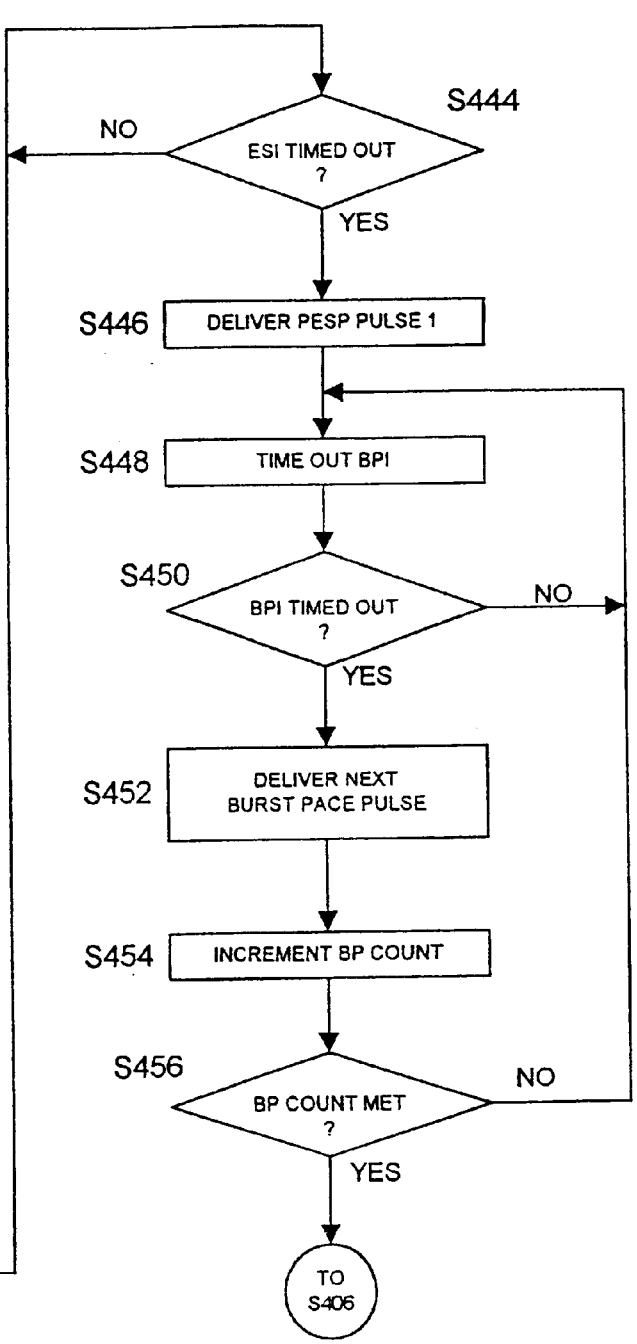

S414 - MR PARAMETER

S414 - MR PARAMETER

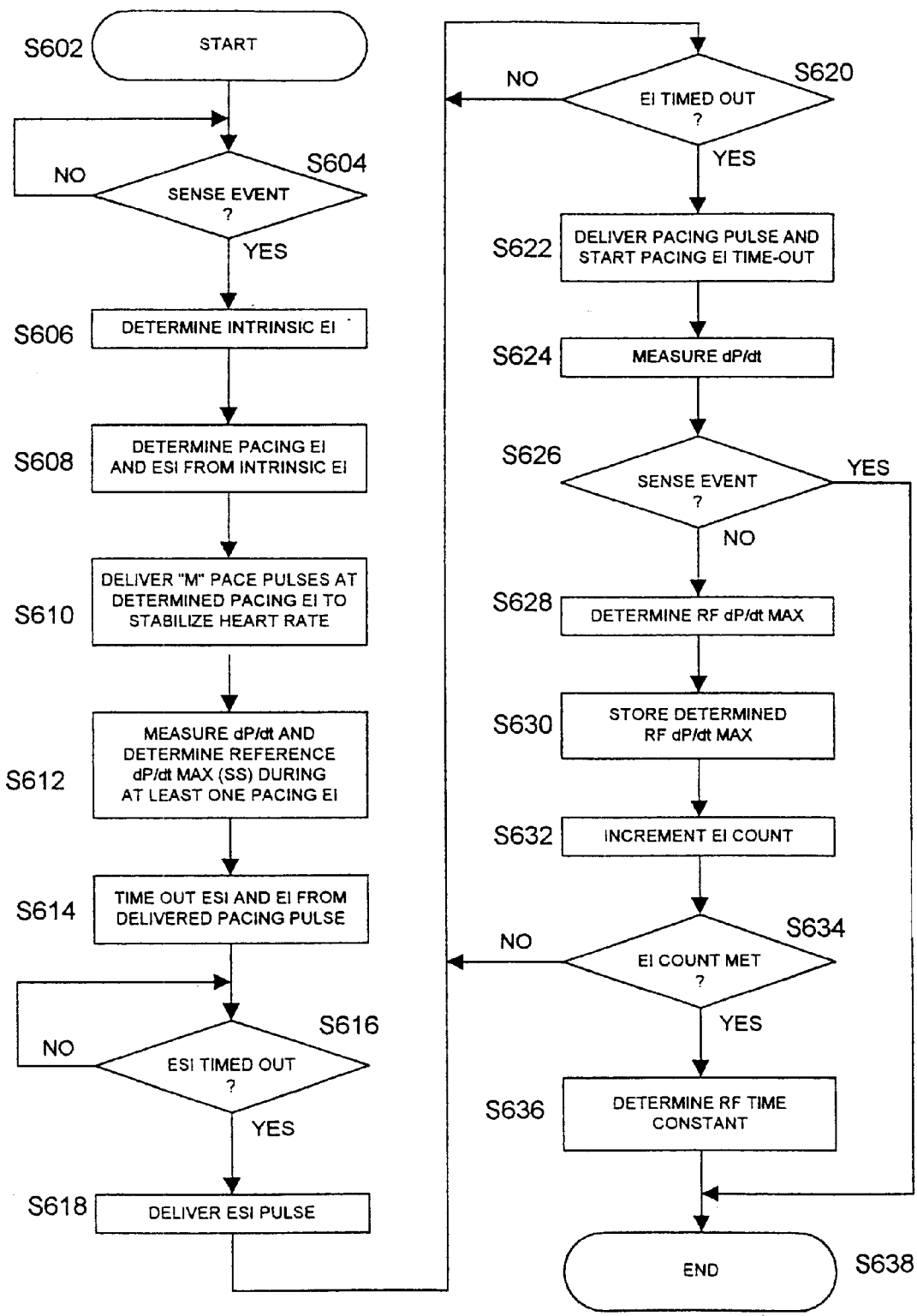

$$\frac{\text{RV dP/dt MIN (ES)}}{\text{RV diastolic parameter (SS)}}$$

$$\frac{\text{RV systolic parameter (ES)}}{\text{RV systolic parameter (SS)}}$$

Extra Systolic Interval

IMPLANTABLE MEDICAL DEVICE FOR TREATING CARDIAC MECHANICAL DYSFUNCTION BY ELECTRICAL STIMULATION

CROSS-REFERENCE TO RELATED APPLICATION

Reference is hereby made to commonly assigned, co-pending U.S. patent application Ser. No. (P-9633.00) filed on even date herewith entitled IMPLANTABLE MEDICAL DEVICE FOR MONITORING CONGESTIVE HEART FAILURE by Lawence J. Mulligan et al.

FIELD OF THE INVENTION

The present invention relates generally to implantable medical devices and more specifically to monitoring signs of acute or chronic cardiac mechanical dysfunction such as congestive heart failure (CHF) or cardiogenic shock and providing appropriate therapies.

BACKGROUND OF THE INVENTION

Patients suffering from chronic CHF manifest an elevation of left ventricular end-diastolic pressure, according to the well-known heterometric autoregulation principles espoused by Frank and Starling. This may occur while left ventricular end-diastolic volume remains normal due to a decrease in left ventricular compliance concomitant with increased ventricular wall stiffness. CHF due to chronic hypertension, ischemia, infarct or idiopathic cardiomyopathy is associated with compromised systolic and diastolic function involving decreased atrial and ventricular muscle compliance. These may be conditions associated with chronic disease processes or complications from cardiac surgery with or without specific disease processes. Most heart failure patients do not normally suffer from a defect in the conduction system leading to ventricular bradycardia, but rather suffer from symptoms which may include a general weakening of the contractile function of the cardiac muscle, attendant enlargement thereof, impaired myocardial relaxation and depressed ventricular filling characteristics in the diastolic phase following contraction. Pulmonary edema, shortness of breath, and disruption in systemic blood pressure are associated with acute exacerbations of heart failure. All these disease processes lead to insufficient cardiac output to sustain mild or moderate levels of exercise and proper function of other body organs, and progressive worsening eventually results in cardiogenic shock, arrhythmias, electromechanical dissociation, and death.

Such patients are normally treated with drug therapies, including digitalis, which may lead to toxicity and loss of effectiveness. Many inotropic drugs have recently become available, targeted at various receptors in the myocyte and designed for the purpose of directly stimulating cardiac tissue in order to increase contractility. However, there exist many possible undesirable side effects, in addition to the fact that these drugs do not always work for their intended purpose. This is especially characteristic of the patient suffering from end-stage heart failure.

In the early days of implantable cardiac pacing, it was observed that paired pacing (two or more closely spaced pacing pulses delivered at the time-out of an escape interval) and triggered or coupled pacing (one or more pacing pulses delivered following the detection of a P-wave or R-wave terminating an escape interval) with relatively short interpulse intervals (150 to 250 milliseconds in dogs and about 300 milliseconds in human subjects) beneficially slowed heart rate and increased cardiac output. The result of the second pulse, applied within the relative refractory period of the first paced or spontaneous depolarization, is to prolong the refractory period and effect a slowing of the heart rate from its spontaneous rhythm without an attendant mechanical myocardial contraction. This slowing effect has been employed since that time in many applications, including the treatment of atrial and ventricular tachycardias, where a single pulse or a burst of pulses are coupled to a spontaneous tachycardia event with a coupling interval that is shorter than and can be set as a fraction of the tachycardia interval as taught, for example, in U.S. Pat. Nos. 3,857,399 and 3,939,844. The slowing of the heart rate by coupled pacing is accompanied by the ability to increase or decrease the rate with subsequent coupled pacing within wide limits.

Paired and coupled stimulation of a heart chamber also cause a potentiation of contractile force effect through a phenomenon known as post-extrasystolic potentiation (PESP) described in detail in commonly assigned U.S. Pat. No. 5,213,098. The force of contraction of the heart is increased during the heart cycle that the paired or coupled stimulation is applied, and the increase persists but gradually diminishes over a number of succeeding heart cycles. Other measurable PESP effects that also persist but gradually decline over a number of heart cycles include changes in the peak systolic blood pressure, the rate of contraction of the ventricular muscle with a resulting increase of the rate of rise of intraventricular pressure (dP/dt), an increase in coronary blood flow, and an increase in the oxygen uptake of the heart per beat. Investigators observed that PESP was accompanied by an increase in the myocardial oxygen consumption of 35% to 70% as compared with single pulse stimulation at the same rate and was associated with a significant improvement in ejection fraction. The addition of a third stimulus increased the myocardial oxygen uptake even further without any attendant observed increase in cardiac contractile force. The alterations in coronary flow roughly parallel the oxygen consumption of the heart as observed in such studies.

The marked potentiation effect produced by paired stimulation led certain investigators to speculate that PESP stimulation would be beneficial in treating heart failure in humans and conducted studies using the technique in the treatment of acute heart failure induced in dogs. Improvements in left ventricular performance and cardiac output produced by such paired pacing in these dogs was observed by several investigators. In other studies conducted on relatively normal dogs' hearts, it was confirmed that paired pacing offered no increase in cardiac output, most likely due to reflex compensation. Early investigators conducted a large number of animal and human studies employing paired and coupled stimulation of the atrial and ventricular chambers, and medical devices were made available by Medtronic, Inc. and other companies in an effort to employ the PESP effect. However, it was realized that the application of closely timed paired and coupled pacing pulses, particularly the high energy pacing pulses that were employed at that time in implantable pacemakers, could trigger a tachyarrhythmia in patient's hearts that were susceptible. The efforts to capitalize on the PESP effects were largely abandoned. A history of the investigations and studies conducted is set forth in the above-referenced '098 patent.

Since dual chamber pacing was developed, conventional, atrioventricular (AV) synchronous pacing systems, including DDD and DDDR pacing systems, marketed by Medtronic, Inc. and other companies, have also been prescribed for treatment of CHF as well as a variety of bradycardia conditions. Certain patient groups suffering heart failure symptoms with or without bradycardia tend to do much better hemodynamically with AV synchronous pacing due to the added contribution of atrial contraction to ventricular filling and subsequent contraction. However, fixed or physiologic sensor driven rate responsive pacing in such patients does not always lead to improvement in cardiac output and alleviation of the symptoms attendant to such disease processes because it is difficult to assess the degree of compromise of cardiac output caused by CHF and to determine the pacing parameters that are optimal for maximizing cardiac output. The magnitude of the AV delay is one factor that requires obtaining pressure data involving an extensive patient work-up as set forth in commonly assigned U.S. Pat. No. 5,626,623.

The above-referenced '098 patent discloses PESP cardiac pacing energy stimulator for applying paired and/or triggered pacing stimulation pulses to the right atrium and/or ventricle incorporating one or more sensors and signal processing circuitry for controlling the frequency of or number of heart cycles between periodic delivery of triggered or paired pacing to induce and optimize the PESP effect for the treatment of CHF or other cardiac dysfunctions. A first sensor, e.g., a ventricular or arterial blood pressure or flow sensor, is employed to monitor the performance of the heart and to develop a cardiac performance index (CPI). A second sensor, e.g., an oxygen saturation sensor positioned in the coronary sinus, is employed to monitor cardiac muscle stress and develop a cardiac stress index (CSI) to balance performance and stress. The disclosed PESP stimulator may be incorporated into a dual chamber (DDD) pacing system with or without physiologic rate control and with or without backup cardioversion/defibrillation therapy capabilities or in a separate, single purpose device. The PESP stimulator has particular application in atrial stimulation for augmenting filling of the ventricles.

A series of PCT publications including, for example, PCT WO 97/25098 describe the application of one or more "non-excitatory" anodal or cathodal stimulation pulses to the heart and maintain that improvements in LV performance may be realized without capturing the heart. In a further commonly assigned U.S. Pat. No. 5,800,464, sub-threshold anodal stimulation is provided to the heart to condition the heart to mechanically respond more vigorously to the conventional cathodal supra-threshold pacing pulses.

Thus, various stimulation regimens have been proposed for the treatment of heart failure including CHF which involve application of supra-threshold and/or sub-threshold stimulation paired or coupled pacing pulses or pulse trains. Moreover, various electrodes have been proposed for single site and multi-site delivery of the stimulation pulses to one or more heart chamber in the above-referenced patents and publications. However, it remains difficult to economically determine appropriate candidates that would benefit from such stimulation and to measure the efficacy of a given stimulation regimen and/or electrode array. Extensive catheterization procedures must be conducted of a heart failure patient to determine if he or she is a candidate for implantation of such a system. Then, the efficacy of any given treatment must be assessed at implantation and in periodic post-implant follow-up clinical tests. The patient work-up and follow-up testing must take into account or simulate known patient activities, patient posture, and whether the patient is awake or asleep in order to be representative of the heart failure condition over a daily time span.

Physiologic and device operating data gathering capabilities have been included in modern implantable cardiac pacemakers and implantable cardioverter/defibrillators (ICDs) in order to provide a record of bradycardia or tachyarrhythmia episodes and the response to same provided by the pacemaker or ICD. The stored physiologic device operations and patient data as well as real-time EGM data can be uplink telemetered to an external programmer for display and analysis by medical heath care providers, as is well known in the art.

In addition, implantable cardiac monitors have been clinically used or proposed for use for monitoring hemodynamic and electrical signals of a patient's heart that do not presently include any stimulation capabilities, e.g., cardiac pacing or cardioversion/defibrillation. Such implantable monitors are implanted in patients to develop data over a longer time period than in the clinical setting that can be retrieved in the same manner and used to diagnose a cardiac dysfunction, including CHF, that manifests itself sporadically or under certain loads and stresses of daily living.

One such implantable EGM monitor for recording the cardiac electrogram from electrodes remote from the heart as disclosed in commonly assigned U.S. Pat. No. 5,331,966 and PCT publication WO 98/02209 is embodied in the Medtronic® REVEAL® Insertable Loop Recorder having spaced housing EGM electrodes. More elaborate implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have also been proposed. The Medtronic® CHRONICLE® IHM is an example of such a monitor that is coupled through a lead of the type described in commonly assigned U.S. Pat. No. 5,564,434 having capacitive blood pressure and temperature sensors as well as EGM sense electrodes. Such implantable monitors when implanted in patients suffering from cardiac arrhythmias or heart failure accumulate date and time stamped data that can be of use in determining the condition of the heart over an extended period of time and while the patient is engaged in daily activities.

A CHF monitor/stimulator is disclosed in commonly assigned U.S. Pat. No. 6,104,949 that senses the trans-thoracic impedance as well as patient posture and provides a record of same to diagnose and assess the degree and progression of CHF. The sensed trans-thoracic impedance is dependent on the blood or fluid content of the lungs and assists in the detection and quantification of pulmonary edema symptomatic of CHF. Trans-thoracic impedance is affected by posture, i.e. whether the subject is lying down or standing up, and the sensed trans-thoracic impedance is correlated to the output of the patient posture detector to make a determination of presence of and the degree of pulmonary edema for therapy delivery and/or physiologic data storage decisions.

A monitor/stimulator is disclosed in U.S. Pat. No. 5,417,717, that monitors and assesses level of cardiac function then permits a physician to arbitrate the therapy mode, if therapy is indicated. The monitor stimulator assesses impedance, EGM, and/or pressure measurements, and then calculates various cardiac parameters. The results of these calculations determine the mode of therapy to be chosen. Therapy may be administered by the device itself or a control signal may be telemetered to various peripheral devices aimed at enhancing the heart's function. Alternatively, the device may be programmed to monitor and either store or telemeter information without delivering therapy.

Particularly, the implantable monitor/stimulator monitors conventional parameters of cardiac function and contractile state, including all phases of the cardiac cycle. Thus, assessments of contractile state measured include indices of both cardiac relaxation and contraction. Utilizing the dual source ventricular impedance plethysmography technique described in U.S. Pat. No. 4,674,518, the monitor/stimulator monitors cardiac function by assessing hemodynamic changes in ventricular filling and ejection or by calculating isovolumic phase indices by known algorithms. The primary calculations involve: (1) the time rate of change in pressure or volume, dP/dt or dV/dt, as isovolumic indicators of contractility; (2) ejection fraction as an ejection phase index of cardiac function according to the known quotient of stroke volume divided by end diastolic volume; (3) Maximal elastance, $E_M$; (4) regression slope through maximal pressure-volume points as a further ejection phase index of contractility using the method of Sagawa; (5) stroke work according to the known pressure-volume integration; (6) the time course of minimum (end) diastolic pressure-volume measurements according to the method of Glantz as a measure of diastolic function; and (7) cardiac output calculation according to the known product of heart rate and stroke volume as an index of level of global function.

While measurement and storage of this group of parameters of cardiac function and contractile state can provide valuable information about the state of heart failure, there are other parameters that of even greater value. Momentary changes to a patient's autonomic state can change blood pressure (P), heart rate, and pressure rate of change (dP/dt) contractility measures and not be reflective of a "true" functional state change of the heart. Such momentary changes in autonomic state are caused by postural changes as noted in the above-referenced '949 patent and other movements, such as bending down to pick up an object or suddenly standing up from a sitting or reclining position. It would be desirable to obtain cardiac data that provides an enhanced assessment of cardiac contractile dysfunction state (rather than a measure of pulmonary edema as in the '949 patent) that are less sensitive to such patient movements and posture changes by enhanced signal processing of relatively simple to measure cardiac signals and states.

SUMMARY OF THE INVENTION

In accordance with the present invention, an implantable stimulator and monitor measures a group of parameters indicative of the state of heart failure employing EGM signals, measures of blood pressure including absolute pressure P, developed pressure DP (DP=systolic P−diastolic P), and/or dP/dt, and measures of heart chamber volume (V) over one or more cardiac cycles. These parameters include: (1) relaxation or contraction time constant (tau); (2) mechanical restitution (MR), i.e., the mechanical response of a heart chamber to premature stimuli applied to the heart chamber; (3) recirculation fraction (RF), i.e., the rate of decay of PESP effects over a series of heart cycles; and (4) end systolic elastance ($E_{ES}$), i.e., the ratios of end systolic blood pressure P to volume V. These cardiac state parameters are determined periodically regardless of patient posture and activity level. However, certain of the parameters are only measured or certain of the data are only stored when the patient heart rate is regular and within a normal sinus range between programmed lower and upper heart rates.

The implantable stimulator and monitor is operated in a one or more of the measurement modes that, in some instances, require delivery of an extrasystolic (ES) pulse after an extrasystolic interval (ESI) to induce PESP effects that are measured. In the present invention, the PESP capability is also employed to strengthen the cardiac contraction when one or more of the MR, RF, tau, and $E_{ES}$ parameters show that the heart condition has progressed to benefit from increased contractility, decreased relaxation time, and increased cardiac output. In this context, the stimulation therapy is referred to as PESP stimulation or pacing. In accordance with the invention, the effects of the applied PESP stimulation therapy can be observed over time by entering a heart function parameter measuring mode and gathering the parameter data.

Preferably, the parameter data is associated with a date and time stamp and with other patient data, e.g., patient activity level, and the associated parameter data is stored in IMD memory for retrieval at a later date employing conventional telemetry systems. Incremental changes in the parameter data over time, taking any associated time of day and patient data into account, provide a measure of the degree of change in the condition of the heart.

The present invention combines these approaches, rendering a device that detects and monitors levels of cardiac function and delivers or modifies a therapy on the basis of this monitored information. The primary mode of delivery is direct electrical stimulation, resulting in improved contractility, relaxation, pressures or cardiac output.

The implantable stimulator and monitor that is capable of performing these functions comprises an implantable pulse generator (IPG) and lead system extending into operative relation with at least one and preferably multiple heart chambers for electrical sensing and stimulation, blood pressure measurement and chamber volumetric measurement during contraction and relaxation. The IPG has a sense amplifier for each heart chamber of interest that is coupled through a lead conductor with electrical stimulation/sense electrodes for sensing cardiac electrical heart signals originating in or traversing that heart chamber so that the sense amplifier can detect a P-wave in an atrial chamber or R-wave in a ventricular chamber. The IPG has timing circuitry for timing out atrial and/or ventricular escape intervals and the ESI of coupled or paired PESP stimulating pulse(s). The IPG has a pulse generator coupled with at least one stimulation/sense electrode for delivering pacing pulses and PESP stimulation pulses to each heart chamber of interest. The IPG has blood pressure signal processing circuitry coupled through lead conductors with a blood pressure sensor located in a distal lead section in or in operative relation to each heart chamber of interest for deriving blood pressure P and dP/dt samples. The IPG also has volume determining circuitry coupled with a volumetric sensor located in or in relation with each heart chamber of interest for deriving a signal representative of heart chamber volume V. The volumetric sensor preferably comprises a set of impedance sense electrodes located along a single impedance lead or on a plurality of impedance leads, and the volume determining circuitry coupled to the impedance sensor electrodes detects impedance between selected electrode pairs. The impedance sense electrodes are distributed about the heart chamber such that the distance between the separated electrodes and the measured impedance changes with contraction and relaxation of the heart chamber walls.

The implantable stimulator and monitor can be embodied into a single chamber, dual chamber or multi-chamber rate responsive pacemaker for providing bradycardia pacing when intrinsic sinus heart rate falls below a programmed lower HR. Or, the implantable stimulator and monitor can be embodied into an ICD including such single chamber, dual chamber or multi-chamber rate responsive pacing capabilities as well as tachyarrhythmia detection and cardioversion/ defibrillation shock delivery capabilities. In either case, tachycardia detection and anti-tachycardia pacing as well as cardiac resynchronization pacing therapies can also be incorporated.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 4A and 4B constitute a flow chart depicting the monitoring and therapy delivery function of the IMD of FIGS. 1–3, measuring one or more of a group of parameters indicative of the state of heart failure employing cardiac EGM signals, blood pressure P and dP/dt signals and adjusting electrical stimulation therapies accordingly.

FIG. 6 is a flow chart expanding upon steps of FIG. 4 and depicting the steps of deriving the recirculation fraction RF parameter indicative of the heart failure state from certain signals output by a monitoring and pacing channel of FIG. 3;

DETAILED DESCRIPTION OF THE PREFERRED EMBODIMENTS

In the following detailed description, references are made to illustrative embodiments for carrying out the invention. It is understood that other embodiments may be utilized without departing from the scope of the invention.

Figure 22:
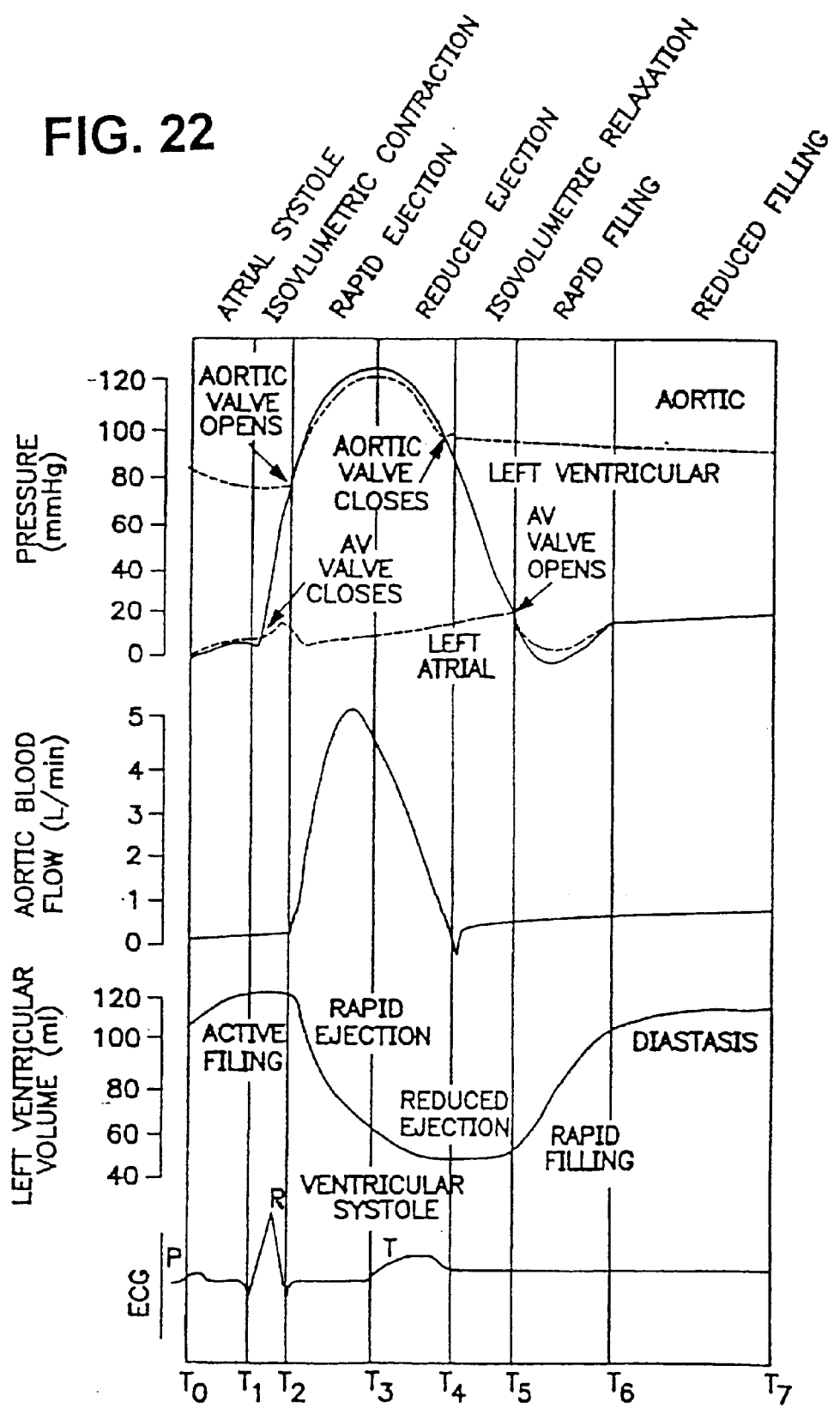
FIG. 22 depicts the relationship of heart chamber EGM, pressure, flow, and volume during a heart cycle.

Before describing the preferred embodiments, reference is made to FIG. 22 reproduced from the above-referenced '464 patent which depicts the electrical depolarization waves attendant a normal sinus rhythm cardiac cycle in relation to the fluctuations in absolute blood pressure, aortic blood flow and ventricular volume in the left heart. The right atria and ventricles exhibit roughly similar pressure, flow and volume fluctuations, in relation to the PQRST complex, as the left atria and ventricles. It is understood that the monitoring and stimulation therapy aspects of this invention may reside and act on either or both sides of the heart. The cardiac cycle is completed in the interval between successive PQRST complexes and following relaxation of the atria and ventricles as the right and left atria re-fill with venous blood and oxygenated blood. In sinus rhythm, the interval between depolarizations may be on the order of 500.0 ms to 1,000.0 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 22, it may be observed that the atrial and ventricular blood pressure changes track and lag the P-waves and R-waves of the cardiac cycle. The time period $T_0$–$T_1$ encompasses the AV interval.

In patients suffering from cardiac insufficiency arising from bradycardia due to an incompetent SA node or AV-block, atrial and/or ventricular conventional pacing may be prescribed to restore a sufficient heart rate and AV synchrony. In FIG. 22, for example, atrial and/or ventricular pacing pulses would precede the P-wave and the deflection of the QRS complex commonly referred to as the R-wave. Cardiac output may be reduced by the inability of the atrial or ventricular myocardial cells to relax following atrial ($T_0$–$T_1$) and ventricular ($T_1$–$T_2$) systolic periods. Prolonged systolic time periods reduce passive filling time $T_4$–$T_7$ as shown in FIG. 22. Thus, the amount of blood expelled from the atria and/or ventricles in the next cardiac cycle may be less than optimum. This is particularly the case with CHF patients or other patients in whom the stiffness of the heart is increased, cardiac filling during the passive filling phase ($T_4$–$T_7$) and during atrial systole ($T_0$–$T_1$) is significantly limited.

It will be appreciated from the following description that the monitor/therapy delivery IMD of the present invention may be utilized to obtain the aforementioned parameters as stored patient data over a period of time and to deliver therapies for treating the heart failure. The physician is able to initiate uplink telemetry of the patient data in order to review it to make an assessment of the heart failure state of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, including PESP stimulation, and pacing therapies including single chamber, dual chamber and multi-chamber (bi-atrial and/or bi-ventricular) pacing. Moreover, in patient's prone to malignant tachyarrhythmias, the assessment of heart failure state can be taken into account in setting parameters of detection or classification of tachyarrhythmias and the therapies that are delivered.

Accordingly, an embodiment of the invention is disclosed in detail in the context of a multi-chamber pacing system that is modified to derive the aforementioned parameters indicative of cardiac mechanical dysfunction from sensors, sense electrodes and electrical stimulation electrodes located in operative relation to one or more heart chamber. This embodiment of the invention may be programmed to operate as an AV sequential, bi-atrial and bi-ventricular, pacing system operating in demand, atrial tracking, and triggered pacing for restoring synchrony in depolarizations and contraction of left and right ventricles in synchronization with atrial sensed and paced events for treating CHF and/or bradycardia. This embodiment of the invention is therefore programmable to operate as a two, three or four channel pacing system having an AV synchronous operating mode for restoring upper and lower heart chamber synchronization and right and left atrial and/or ventricular chamber depolarization synchrony. However, it will be understood that only certain of the components of the complex multi-chamber pacing system described below can be selectively programmed to function or physically only incorporated into a simpler, single chamber, monitoring/stimulation system for deriving the parameters indicative of heart failure state.

Figure 1:
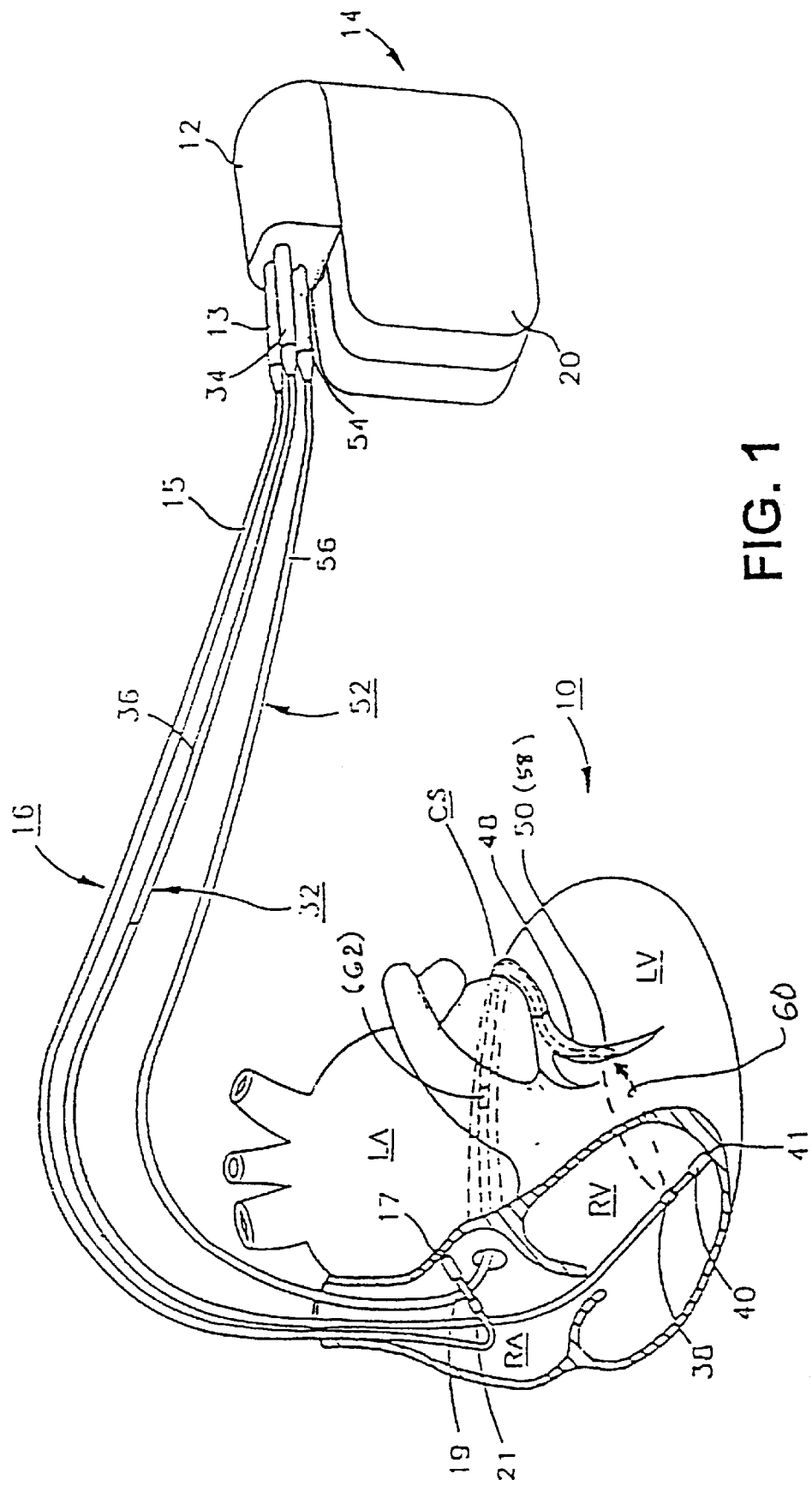
FIG. 1 is a schematic diagram depicting a multi-channel, atrial and bi-ventricular, monitoring/pacing IMD in which the present invention is preferably implemented.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiority into branches of the great vein. The cardiac cycle commences normally with the generation of the depolarization impulse at the SA Node in the right atrial wall. The impulse then conducts through the right atrium by way of Intermodal Tracts, and conducts to the left atrial septum by way of Bachmann's Bundle. The RA depolarization wave reaches the Atrio-ventricular (AV) node and the atrial septum within about 40 msec and reaches the furthest walls of the RA and LA within about 70 msec. Approximately 50 ms following electrical activation, the atria contract. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node conducts down the bundle of His in the intraventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent to the RV or LV exceeds a threshold amplitude, it is detected as a sensed R-wave. Although the location and spacing of the external ECG electrodes or implanted unipolar ventricular pace/sense electrodes has some influence on R-wave sensing, the normal R-wave duration does not exceed 80 msec as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The normal electrical activation sequence becomes highly disrupted in patients suffering from advanced CHF and exhibiting Intra-atrial conduction delay (IACD), Left Bundle Branch Block (LBBB), Right Bundle Branch Block (RBBB), and/or Intraventricular Conduction Delay (IVCD). These conduction defects give rise to great asynchrony between RV activation and LV activation. Inter-ventricular asynchrony can range from 80 to 200 msec or longer. In RBBB and LBBB patients, the QRS complex is widened far beyond the normal range to between 120 msec and 250 msec as measured on surface ECG. This increased width demonstrates the lack of synchrony of the right and left ventricular depolarizations and contractions.

FIG. 1 also depicts an implanted, multi-channel cardiac pacemaker of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the great vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiority from the great vein 48.

Preferably, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV as described further below.

Moreover, in a four chamber embodiment, LV CS lead 52 could bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate.

In addition, as described further below, each of the leads could carry a pressure sensor for developing systolic and diastolic pressures and a series of spaced apart impedance sensing leads for developing volumetric measurements of the expansion and contraction of the RA, LA, RV and LV.

Figure 2:
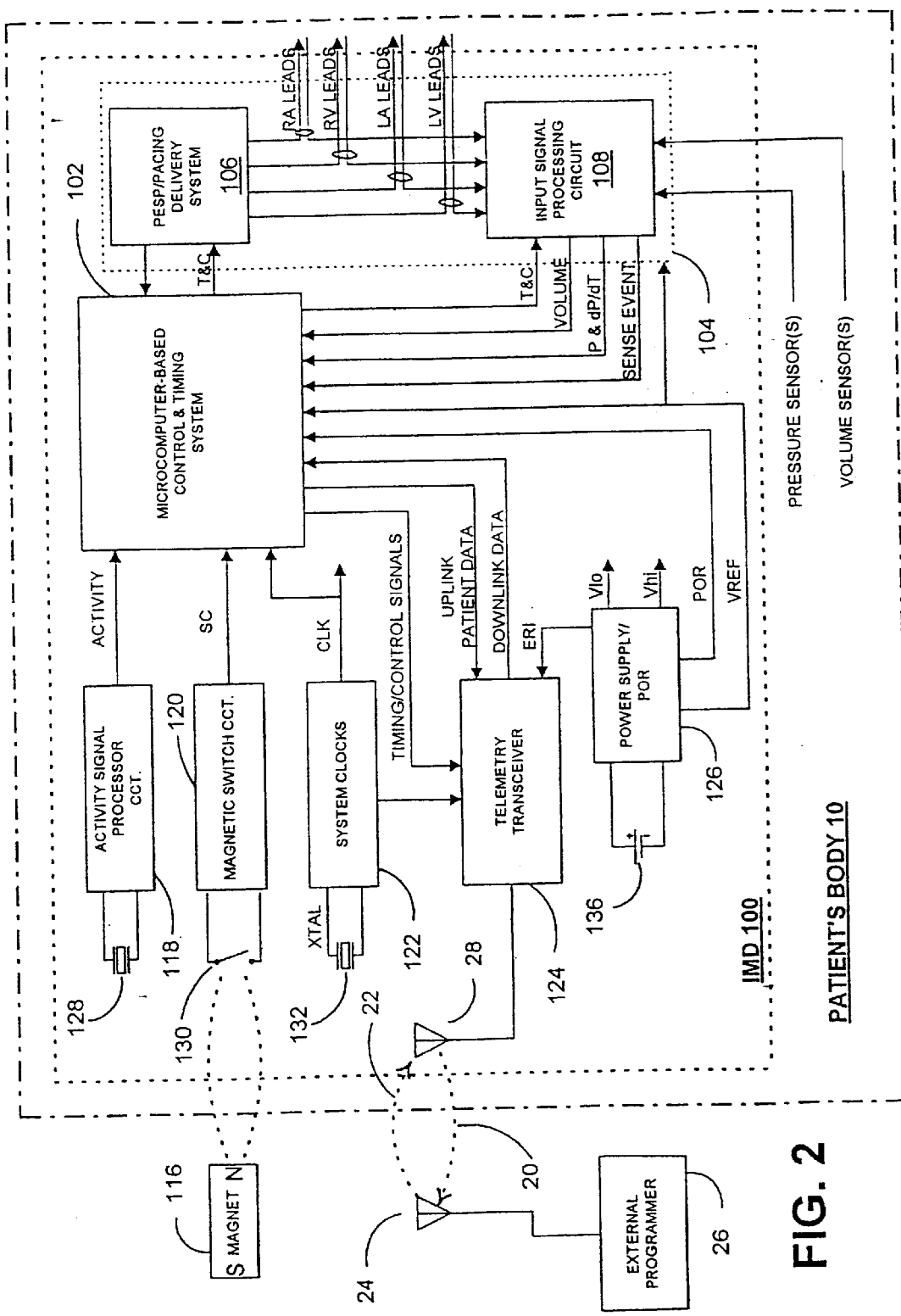
FIG. 2 is a simplified block diagram of one embodiment of IPG circuitry and associated leads employed in the system of FIG. 1 enabling selective therapy delivery and heart failure state monitoring in one or more heart chamber.

FIG. 2 depicts a system architecture of an exemplary multi-chamber monitor/sensor 100 implanted into a patient's body 10 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed micro-computer.

The multi-chamber monitor/sensor 100 also typically includes patient interface circuitry 104 for receiving signals from sensors and pace/sense electrodes located at specific sites of the patient's heart chambers and/or delivering PESP stimulation to derive heart failure parameters or a pacing therapy to the heart chambers. The patient interface circuitry 104 therefore comprises a PESP stimulation delivery system 106 optionally including pacing and other stimulation therapies and a physiologic input signal processing circuit 108 for processing the blood pressure and volumetric signals output by sensors. For purposes of illustration of the possible uses of the invention, a set of lead connections are depicted for making electrical connections between the therapy delivery system 106 and the input signal processing circuit 108 and sets of pace/sense electrodes located in operative relation to the RA, LA, RV and LV.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Or the therapy delivery system 106 can be configured as a drug pump for delivering drugs into the heart to alleviate heart failure or to operate an implantable heart assist device or pump implanted in patients awaiting a heart transplant operation.

A battery provides a source of electrical energy to power the multi-chamber monitor/sensor operating system including the circuitry of multichamber monitor/sensor 100 and to power any electromechanical devices, e.g., valves, pumps, etc. of a substance delivery multi-chamber monitor/sensor, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 2.

In addition, in certain multi-chamber monitor/sensors, an audible patient alert warning or message is generated by a transducer 128 when driven by a patient alert driver 118 to advise of device operations, battery power level or a monitored patient condition. In ids, the patient may be warned of the detection of a malignant tachyarrhythmia and the imminent delivery of a cardioversion/defibrillation shock to enable the patient to assume a resting position prior to delivery.

Virtually all current electronic multi-chamber monitor/sensor circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the multi-chamber monitor/sensor 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber monitor/sensor 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the multi-chamber monitor/sensor 100, uplink and downlink telemetry capabilities are provided to enable communication with either a remotely located external medical device or a more proximal medical device on the patient's body or another multi-chamber monitor/sensor in the patient's body as described above with respect to FIGS. 1 and 2. The stored physiologic data of the types described above as well as real-time generated physiologic data and non-physiologic data can be transmitted by uplink RF telemetry from the multi-chamber monitor/sensor 100 to the external programmer or other remote medical device 26 in response to a downlink telemetered interrogation command. The real-time physiologic data typically includes real time sampled signal levels, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ids, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/sensor thus develops a variety of such real-time or stored, physiologic or non-physiologic, data, and such developed data is collectively referred to herein as "patient data".

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal processing channel for sensing and processing a sensor derived signal from a physiologic sensor located in relation to a heart chamber or elsewhere in the body.

Figure 3:
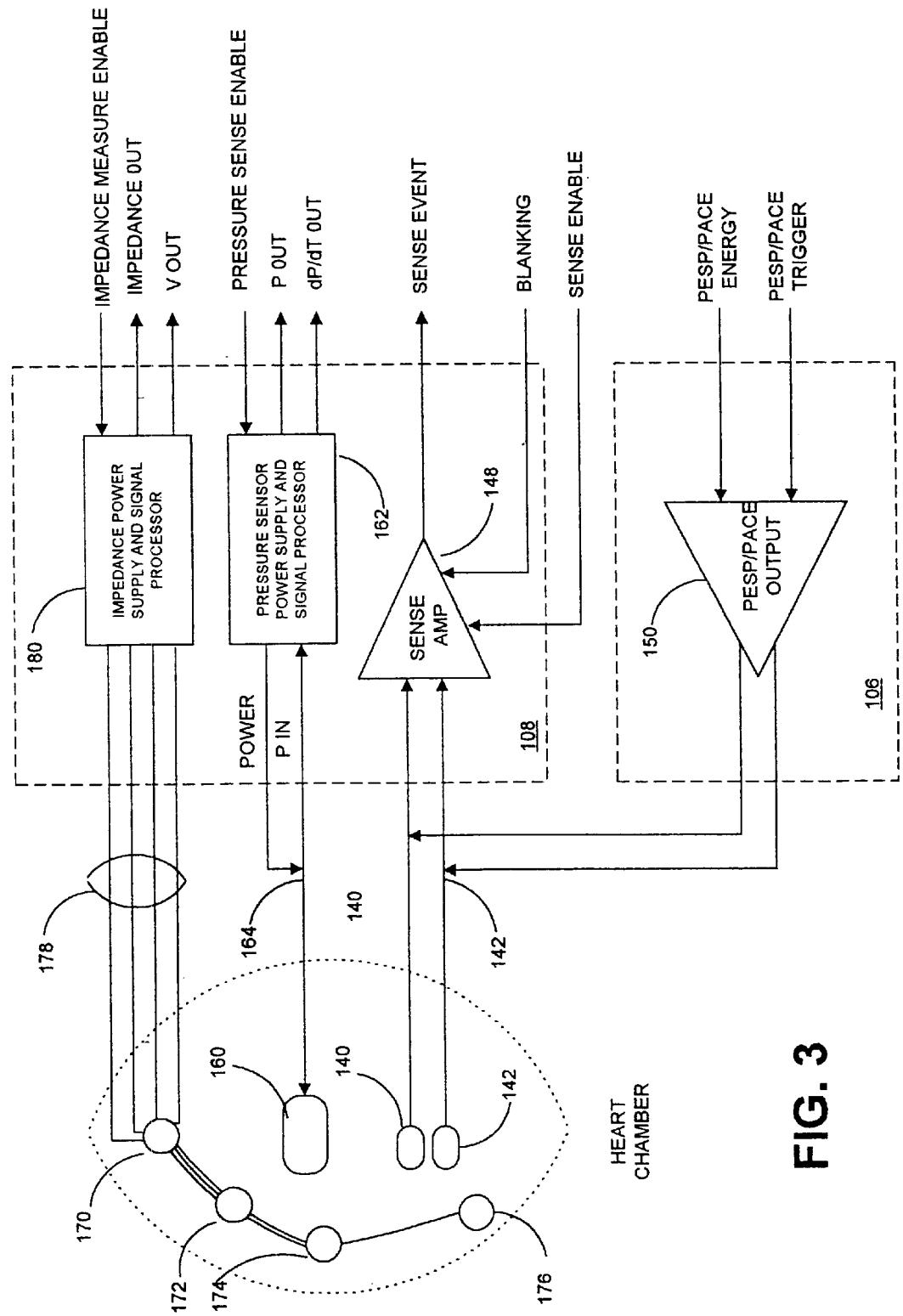
FIG. 3 is a simplified block diagram of a single monitoring and pacing channel for deriving pressure, impedance and cardiac EGM signals employed in monitoring CHF and optionally pacing the heart and delivering PESP therapy in accordance with the present invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart chamber.

The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled as described below in reference to the measurement of the parameters of heart failure. The blanking signal is provided by control and timing system 102 upon delivery of a pacing or PESP pulse or pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art. The control and timing system responds to non-refractory sense events by restarting an escape interval (EI) timer timing out the EI for the heart chamber, in a manner well known in the pacing art.

The pair of pace/sense electrodes 140, 142 are also coupled through lead conductors 144 and 146, respectively, to the output of a pulse generator 150. The pulse generator 150, within PESP/pacing delivery system 106, selectively provides a pacing pulse to electrodes 140, 142 in response to a PESP/PACE trigger signal generated at the time-out of the EI timer within control and timing system 102 in a manner well known in the pacing art. Or, the pulse generator 150 selectively provides a PESP pulse or pulse train to electrodes 140, 142 in response to a PESP/PACE trigger signal generated at the time-out of an ESI timer within control and timing system 102 in the manner described in the above-referenced '098 patent to cause the heart chamber to contract more forcefully, the increased force depending upon the duration of the ESI.

The pressure sensor 160 is coupled to a pressure sensor power supply and signal processor 162 within the input signal processing circuit 108 through a set of lead conductors 164 that convey power to the pressure sensor 160 and sampled blood pressure P signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure P, developed pressure DP and pressure rate of change dP/dt sample values can be developed by the pressure sensor power supply and signal processor 162 or by the control and timing system 102 for storage and processing as described further below. The pressure sensor 160 and a pressure sensor power supply and signal processor 162 may take the form disclosed in commonly assigned U.S. Pat. No. 5,564,434.

The set of impedance electrodes 170, 172, 174 and 176 is coupled by a set of conductors 178 and is formed as a lead of the type described in the above-referenced '717 patent that is coupled to the impedance power supply and signal processor 180. Impedance-based measurements of cardiac parameters such as stroke volume are known in the art as described in the above-referenced '417 patent which discloses an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

A measure of heart chamber volume V is provided by the set of impedance electrodes 170, 172, 174 and 176 when the impedance power supply and signal processor 180 is enabled by an impedance measure enable signal provided by control and timing system 102. A fixed current carrier signal is applied between the pairs of impedance electrodes and the voltage of the signal is modulated by the impedance through the blood and heart muscle which varies as distance between the impedance electrodes varies. Thus, the calculation of the heart chamber volume V signals from impedance measurements between selected pairs of impedance electrodes 170, 172, 174 and 176 occurs during the contraction and relaxation of the heart chamber that moves the spaced apart electrode pairs closer together and farther apart, respectively, due to the heart wall movement or the tidal flow of blood out of and then into the heart chamber. Raw signals are demodulated, digitized, and processed to obtain an extrapolated impedance value. When this value is divided into the product of blood resistivity times the square of the distance between the pairs of spaced electrodes, the result is a measure of instantaneous heart chamber volume V within the heart chamber.

Figure 4A:
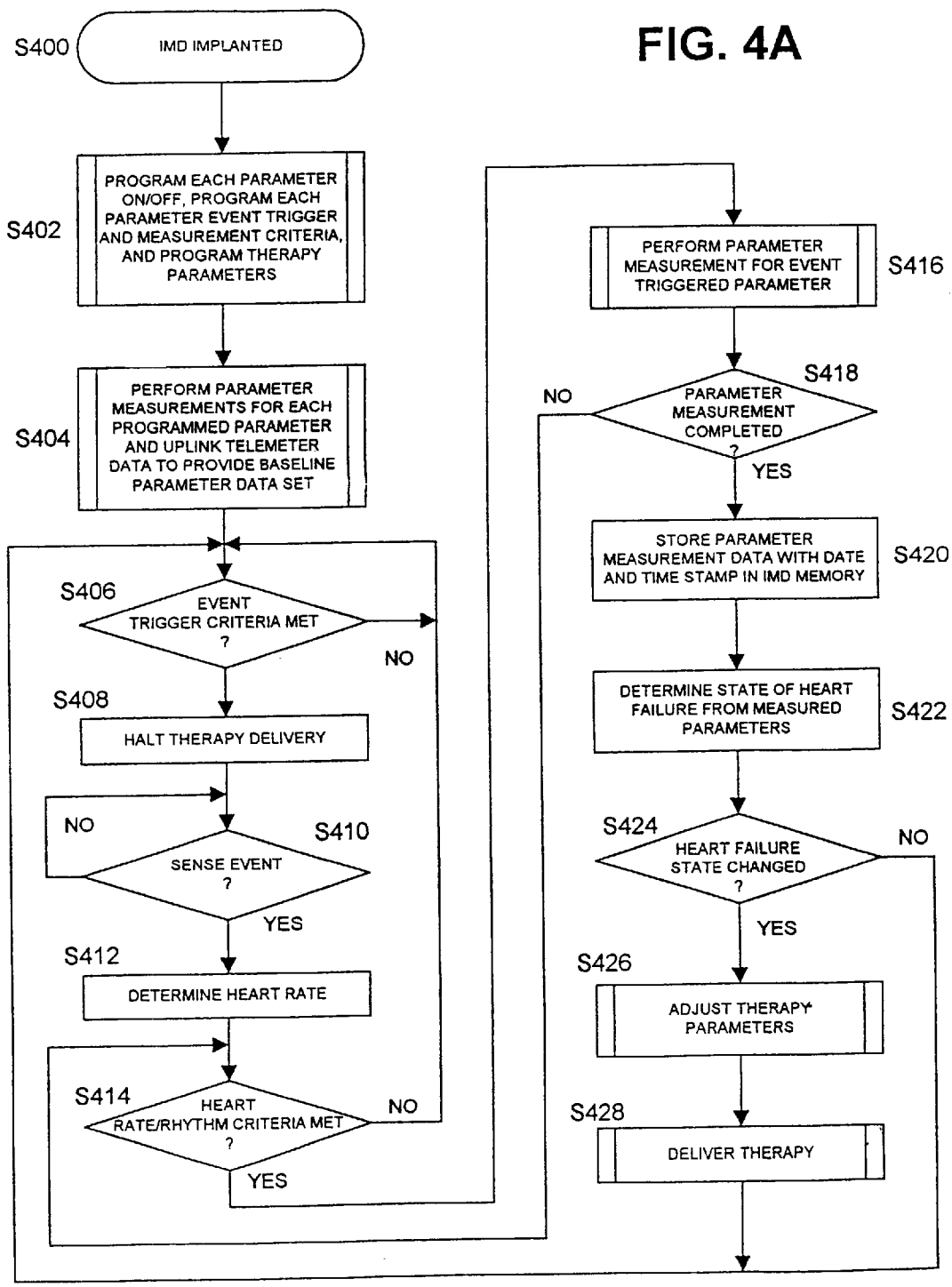

In accordance with the present invention, the IMD measures a group of parameters indicative of the state of heart failure employing EGM signals, measures of absolute blood pressure P and/or dP/dt, and measures of heart chamber volume V over one or more cardiac cycles. FIG. 4 sets forth the overall operating algorithm of the IMD, and FIGS.

5A–5C, 6, 7, and 8 set forth particular parameter measurement and calculation algorithms selectively incorporated into the overall operating algorithm that are all carried out in the microcomputer based control and timing system 102. FIGS. 5A–5C, 6, 7, and 8 depict the steps of deriving the RF, MR, $E_{ES}$, and tau parameters indicative of the state of heart failure. These parameters are determined periodically throughout each day regardless of patient posture and activity. However, the patient may be advised by the physician to undertake certain activities or movements at precise times of day or to simultaneously initiate the determination of the parameters though use of a magnet or a limited function programmer that is detected by the IMD. Certain of the parameters are only measured or certain of the parameter data are only stored when the patient heart rate is within a normal sinus range between programmed lower and upper heart rates and the heart rhythm is relatively stable. The parameter data and related data, e.g., heart rate and patient activity level, are date and time stamped and stored in IMD memory for retrieval employing conventional telemetry systems. Incremental changes in the stored data over time provide a measure of the degree of change in the heart failure condition of the heart.

FIG. 4 illustrates the overall IMD function from the time of implantation (step S400) and initial programming (steps 402) and baseline parameter measurements (step S404) through successive cycles of gathering parameter data in the IMD (steps S406–S420), uplink telemetry transmission of the accumulated data to an external programmer (step S422) for display and analysis (step S424), leading to possible reprogramming (step S402) and baseline parameter measurement (step S404) to better assess the heart failure state.

Each parameter may be programmed ON or OFF, and a particular event trigger for starting measurement of the programmed ON parameter as well as any specific measurement criteria can be programmed in step S402 using conventional downlink telemetry transmitted commands that are received in the telemetry transceiver 124 and forwarded to the control and timing system 102.

In addition, the physician may initially program the IMD to deliver a stimulation therapy, e.g., periodically delivered PESP stimulation in accordance with the above-referenced '098 patent or sub-threshold anodal stimulation (AS) in accordance with the above-referenced '464 patent in order to enhance cardiac function after step S402, for example. The physician can then later reprogram the therapy based on the accumulated and analyzed parameter data and any indication therein that the heart failure state is changing or not responding to the stimulation therapy. Alternatively, the physician can prescribe a drug therapy and later adjust the drug therapy based upon the accumulated and analyzed parameter data and any indication therein that the heart failure state is changing or not responding to the drug therapy.

The baseline parameter measurements are optionally performed for each programmed ON parameter by invoking the steps of FIGS. 5A–5C, 6, 7, and/or 8, uplink telemetering the parameter data and analyzing the uplink telemetered data n following implant and following subsequent telemetry sessions. The initial and updated baseline parameter measurements can be stored in the IMD memory and/or stored externally in a patient file maintained by the physician with a date and time stamp and other pertinent data, e.g. patient activity level measured by activity signal processor circuit 118 and patient heart rate.

After implant, the programmed ON parameters are measured when an event trigger for the specific parameter occurs and when heart rate and/or rhythm criteria are met as set forth in steps S406–S412. The event criteria of step S406 may be a programmed time or multiple times of every day or specified days of the week or month or the detection of the patient initiated parameter measurement or some other programmed event, e.g., a combination of the time or times of day and a level of patient exercise indicated by the activity signal processor circuit 118.

Typically, the measurement of the listed parameters should take place when the heart rate is in a normal range and is stable within a certain stability tolerance which can both be programmed by the physician and are determined over a series of heart cycles in steps S408–S412 in a manner well known in the art. The measurement of the particular parameter corresponding to the satisfied event criteria takes place in step S414 if the heat rate/stability criteria are satisfied in step S412 or is aborted if the heart rate/stability criteria are not satisfied in step S412.

The heart rate and/or stability continues to be monitored through steps s416 and S412, and the parameter measurement that is commenced in step S414 may also be aborted if the heart rate and/or stability changes such that the heart rate/stability criteria become no longer satisfied in step S412 before the parameter measurement steps are completed. The completed parameter measurement data is stored in IMD memory with a date and time stamp and any other pertinent information, e.g., patient activity level, in step S418. Steps S406 through S418 are repeated each time that the event trigger criteria for a particular parameter measurement are satisfied until the process is interrupted by initiation of a telemetry session by the physician and uplink telemetry transmission of the accumulated parameter data in step S422. The history of the number, times and dates of successive parameter measurements can also be stored in IMD memory, but the stored parameter data and related data may be discarded on a FIFO basis if the memory capacity assigned to such data storage is exceeded.

Collection of MR Parameter Data:

The MR parameter is believed to be a useful indicator of the state of heart failure and can provide an indication of the state of progression or regression of the heart failure through the comparison of MR parameter data collected over time. The time constants for systolic and diastolic MR provide indirect evidence regarding the sarcoplasmic reticular (SR) function. Systolic restitution is dependent on the release of calcium from the SR and diastolic restitution is dependent on the uptake of calcium by the SR.

Figure 5A:
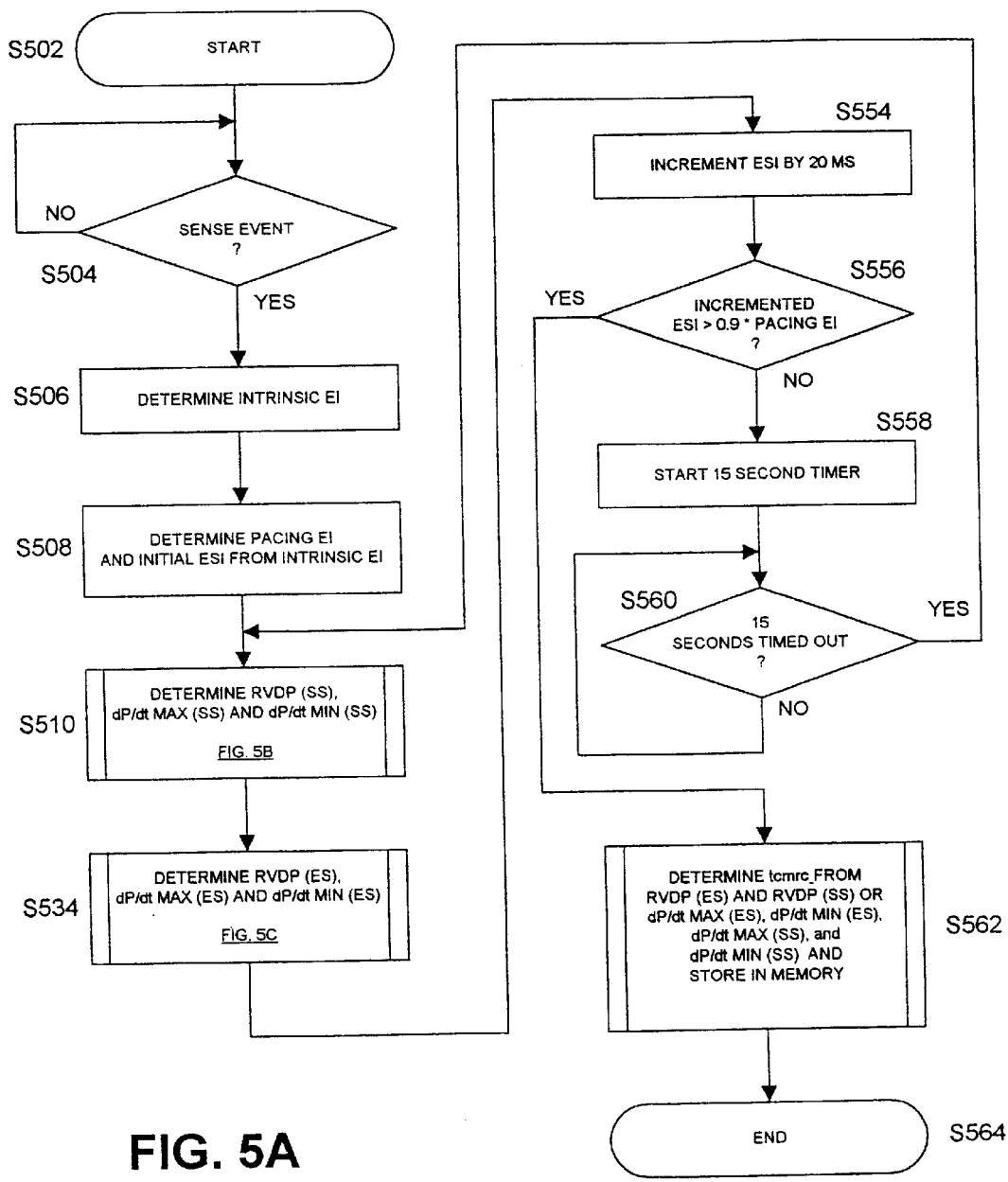
FIGS. 5A–5C is a flow chart expanding upon steps of FIG. 4 and depicting the steps of deriving the mechanical restitution MR parameter indicative of the heart failure state from certain signals output by a monitoring and pacing channel of FIG. 3.
Figure 5B:
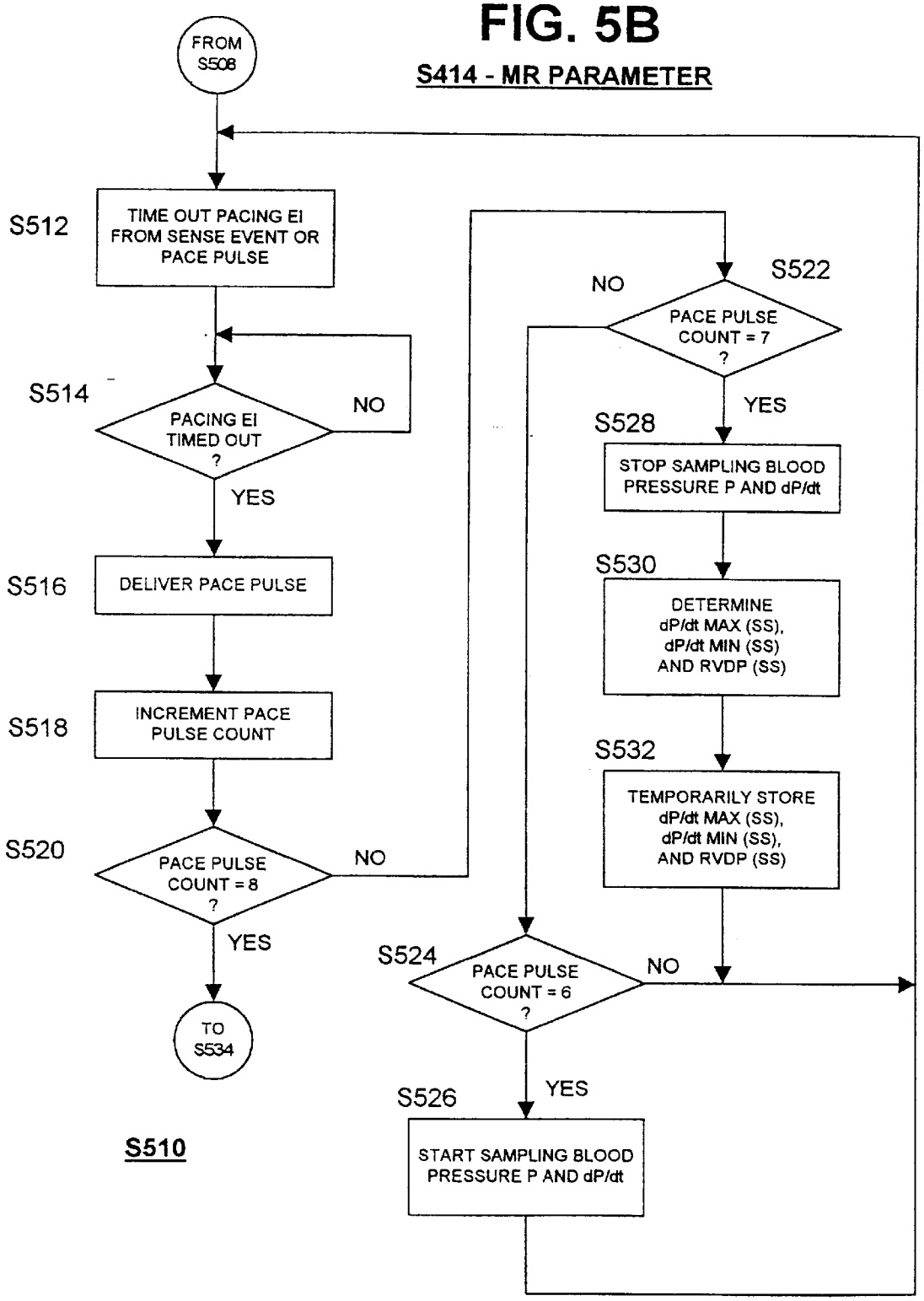
Figure 5C:
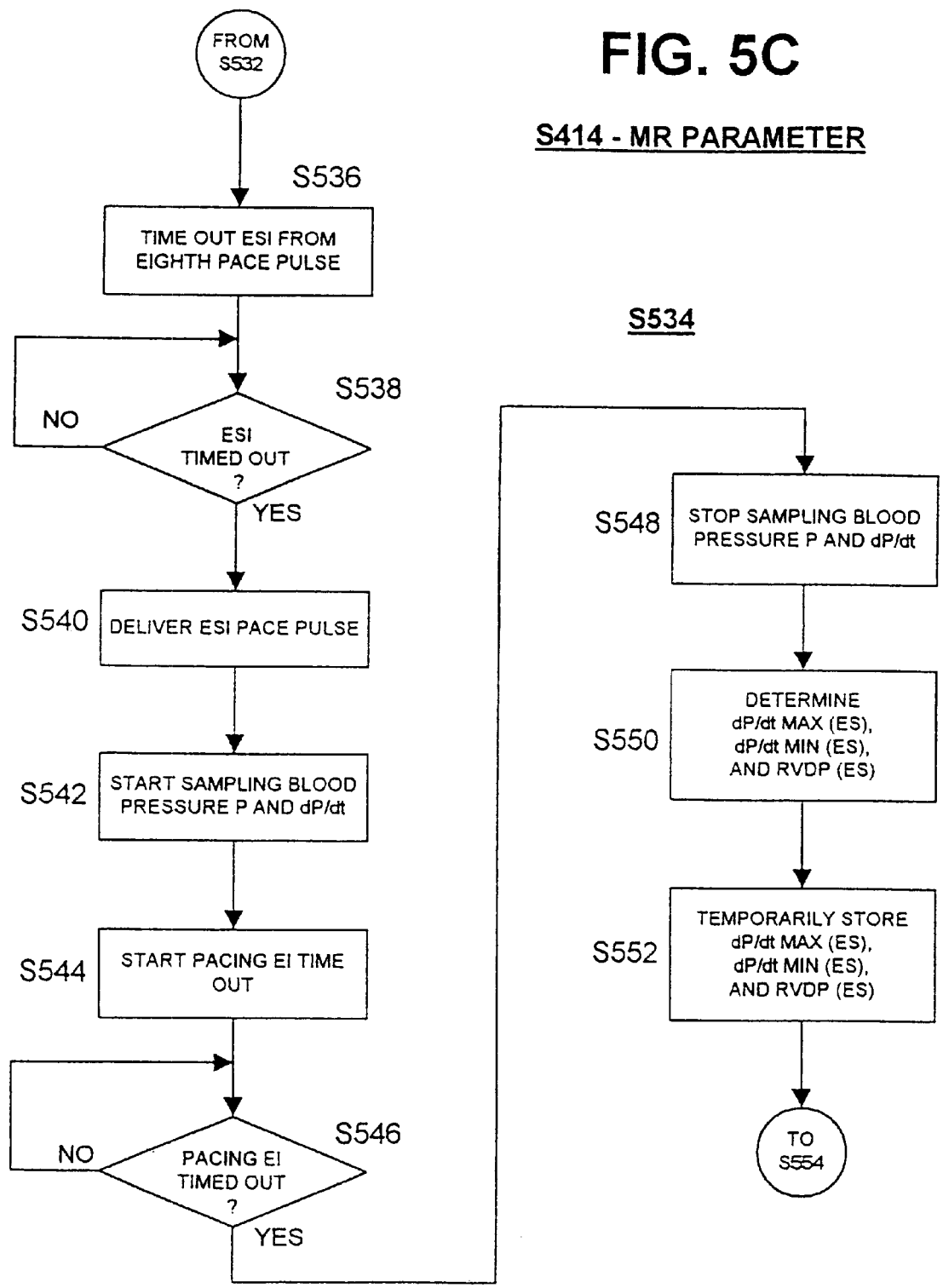

FIGS. 5A–5C depict the steps of determining the MR parameter in step S414 of FIG. 4 in paced heart cycles to ensure steady rate and rate stability. Alternatively, another embodiment of this invention relies on a stable intrinsic rhythm for all but the ESI beats or relies entirely on intrinsic rhythms and spontaneous ectopy for an analogous determination of the MR parameter. Further, although this embodiment relies on pressure as a hemodynamic variable, another embodiment relies on a parameter derived from the volume signal. FIGS. 5B and 5C depict the steps S510 for determining dP/dt MAX (SS) and dP/dt MIN (SS) and/or RVDP (SS) (RVDP=RV systolic pressure−RV diastolic pressure) within a reference steady state (SS) paced heart cycle and S534 for determining dP/dt MAX (ES) and dP/dt MIN (ES) and/or RVDP (ES) within a ESI paced heart cycle of FIG. 5A in greater detail. When the MR parameter measurement is entered, it is necessary to determine the intrinsic EI in steps S504 and S506. In step S508, a pacing EI is calculated that is sufficiently shorter than the intrinsic EI to overdrive pace the heart chamber, and the initial, shortest, ESI is calculated as a fraction of the pacing EI or is determined during the initial baseline programming and measuring steps S402 and S404. The ESI is generally chosen to be as short as possible but to exceed the refractory period of the heart chamber that takes place as the cardiac cells repolarize following a preceding pacing pulse.

The ESI is incremented in step S554, and steps S510 shown in FIG. 5B and S534 shown in FIG. 5C are repeated to derive a series of sets of dP/dt MAX (SS) and dP/dt MIN (SS) and/or RVDP (SS) values and dP/dt MAX (ES) and dP/dt MIN (ES) and/or RVDP (ES) values until the ESI becomes close in length to the pacing EI as determined in step S556. Each repetition of steps S510 through S552 is separated by a rest interval, e.g., 15 seconds, as determined in steps S558 and S560 to allow the mechanical heart function to stabilize.

The determination of dP/dt MAX (SS) and dP/dt MIN (SS) of step S510 is made within a reference paced heart cycle of a series "M" of paced heart cycles. For example, M=8, in FIG. 5B, and the determination of dP/dt MAX (SS) and dP/dt MIN (SS) of step S510 is made in the 6th heart cycle as set forth in steps S512 through S526 of FIG. 5B. The pacing EI determined in step S508 is timed out, and a pacing pulse is delivered at its time-out in steps S514–S516. A pace pulse count is incremented in step S518. The current pace pulse count is examined in steps S520, S522, and S524, and steps S512-S524 are repeated until the pace pulse count equals 6, whereupon the pressure sensor power supply and signal processor 162 is enabled in step S526 to provide the sampled blood pressure P, and dP/dt values throughout the 6th heart cycle. Alternatively, if the pressure sensor power supply and signal processor 162 are always enabled, then the sampled blood pressure P, and dP/dt values output in the 6th heart cycle are used.

The pressure sensor power supply and signal processor 162 is no longer enabled to provide the sampled blood pressure P and dP/dt values or the outputted blood pressure P, and dP/dt values are not used in step S528 when the pace pulse count equals 7 as determined in step S522. The RVDP, dP/dt MAX (SS) and dP/dt MIN (SS) values are determined in step S530 and temporarily stored in step S532.

The determination of dP/dt MAX (ES) and dP/dt MIN (ES) of step S534 after the 8th heart cycle is set forth in steps S536 through S552 of FIG. 5C. The initial ESI calculated in step S508 or the incremented ESI calculated in step S556 of FIG. 5A is timed out in steps S536 and S538. The ES pulse is delivered in step S540, and the pressure sensor power supply and signal processor 162 is enabled to measure the heart chamber blood pressure and provide the P and dP/dt signals to control and timing system 102. The sampled blood pressure P and dP/dt signals are collected in step S542 over the pacing EI that is timed out in steps S544, S546 and S548. Then, the RVDP, dP/dt MAX (ES) and dP/dt MIN (ES) values are determined in step S530 and temporarily stored in step S552.

Then, the MR parameter value $tc_{mrc}$ for the initial or incremented current ESI is determined and stored in IMD memory in step S562. First, each of the dP/dt MAX (ES) values determined in step S550 for each cycle is normalized with respect to the P/dt MAX (SS) determined in step S530, and each of the dP/dt MIN (ES) values determined in step S550 for each cycle is normalized to the dP/dt MIN (SS) determined in step S530. For the systolic function, normalizing is effected by dividing dP/dt MAX (ES) by dP/dt MAX (SS) and multiplying the result by 100. For the diasystolic function, normalizing is effected by dividing dP/dt MIN (ES) by dP/dt MIN (SS) and multiplying the result by 100.

Systolic pulse pressure P and/or developed pressure DP can be normalized in the same manner, if the SS and ES values are also collected in steps S532 and S550.

Figure 14:
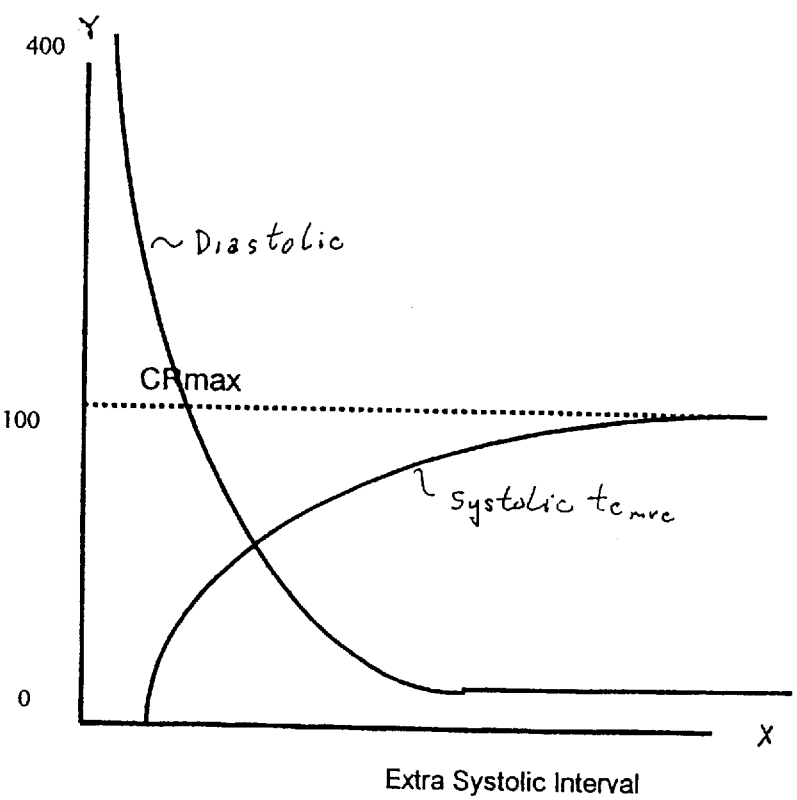
FIG. 14 graphically illustrates the $tc_{mrc}$ of the normalized dP/dt MAX (ES) determined in step S562 in FIG. 5A.

Then, steps S510 through S554 are then performed using the initial ESI to determine the initial MR value $tc_{mrc}$. FIG. 14 graphically illustrates the $tc_{mrc}$ of the normalized dP/dt MAX (ES) determined in step S562 in FIG. 54. After calculating all the normalized values for systolic and diastolic function, the diastolic and systolic time constants ($tc_{mrc}$) are determined in step S562 using the following equations:

Mechanical Restitution:

$$RVDP \text{ or } dP/dt\ MAX = CR_{max} * \{1 - \exp[(ESI_0 - ESI)/tc_{mrc}]\};$$

or when plotted as shown in FIG. 14:

$$Y = CR_{max} * \{1 - \exp[(ESI_0 - X)/tc_{mrc}]\}$$

Where:
RVDP or dP/dt MAX is the normalized value
$CR_{max}$ is the maximal (plateau) of the contractile response
$ESI_0$ is the smallest ESI that produces a mechanical response ("initial ESI")
$tc_{mrc}$ is the time constant of mechanical restitution Relaxation Restitution:
Early phase including data up to the "basic cycle length" (paced rate):

$$R_n = (K_0 - K_a) * \{\exp[(ESI_0 - ESI)/tc_{R1}]\} + K_a$$

or when plotted as shown in FIG. 14:

$$Y = (K_0 - K_a) * \{\exp[(ESI_0 - X)/tc_{R1}]\} + K_a$$

Where:
$R_n$ is the normalized relaxation parameter ($dP/dt_{min}^{-1}$)
$ESI_0$ is the smallest ESI that produces a mechanical response ("initial ESI")
$K_0$ is an estimate of $R_n$ at $ESI_0$
$K_a$ is the plateau asymptote (of the response) during the first phase of
diastolic restitution
$tc_{R1}$ is the time constant of the first phase of diastolic restitution Late Phase:

$$R_n = K_b * \{1 - \exp[(ESI_0 - ESI)/tc_{R2}]\}$$

or when plotted as shown in FIG. 14:

$$Y = K_b * \{1 - \exp[(ESI_0 - X)/tc_{R2}]\}$$

Figure 9:
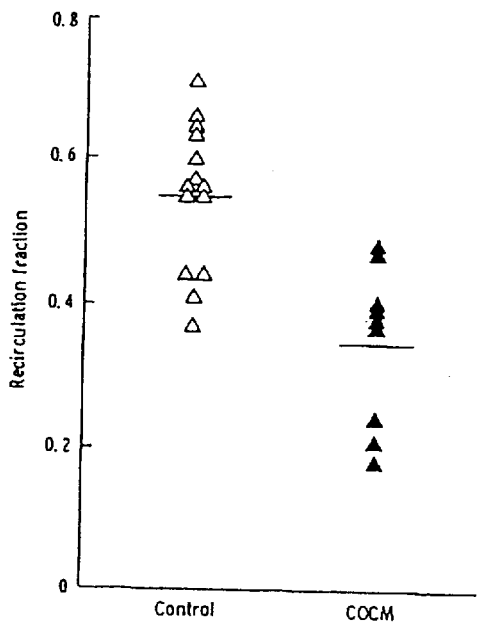
FIG. 9 is a graphical illustration of the recirculation fraction in patients with normal left ventricular function and left ventricular function impaired by dilated cardiomyopathy (COCM)

Where:
$R_n$ is the normalized relaxation parameter ($dP/dt_{min}^{-1}$)
$ESI_0$ is the smallest ESI that produces a mechanical response ("initial ESI")
$K_b$ is the plateau asymptote (of the response) during the late phase of
diastolic restitution
$tc_{R2}$ is the time constant of the second phase of diastolic restitution Collection of RF Parameter Data:
The recirculation fraction RF parameter is believed to be a useful indicator of the state of heart failure and can provide an indication of the state of progression or regression of the heart failure through the comparison of RF parameter data collected over time. The recirculation fraction in patient's with normal left ventricular function (control) and with left ventricular function impaired by dilated cardiomyopathy (COCM) is illustrated in FIG. 9 from Seed, Noble et al., "Relationships Between the Beat-to-Beat Interval and the Strength of Contraction in the Healthy and Diseased Human Heart", CIRCULATION 70:799–805,1984.

The primary information necessary to compute the RF parameter is the measurement of cardiac contractile performance over a consecutive series of cardiac cycles immediately following a cardiac cycle in which a premature intrinsic beat or extrasystole is sensed or immediately following one or more cardiac cycles that an ES pace pulse is delivered at a predetermined ESI. In the preferred embodiment, an electrogram signal (R-wave) is used to define cardiac cycle boundaries and measure intrinsic R—R intervals. Although it is possible to derive cardiac cycle boundaries from mechanical parameters such as ventricular pressure, these parameters are less reliable for premature beats that do not develop much mechanical response.

In addition, an index of the strength of contraction of the heart chamber is measured over a series of succeeding heart cycles to provide a strength of contraction value. The RF parameter of the heart chamber is derived from the accumulated series of strength of contraction values representing the mechanical response of the heart chamber to the electrical stimuli applied to the heart chamber prematurely at expiration of the extrasystolic escape interval. The index can be determined by a number of sensed parameters including blood pressure, chamber volume or a geometry change of the chamber or by the acceleration of the contraction of the chamber through use of an accelerometer. In a preferred embodiment, a continuous RV pressure signal is processed to reveal the maximum dP/dt (dP/dt MAX) over each cardiac cycle. The RVDP or RV systolic pressure alone could alternatively be used. An alternative embodiment relies on an analogous parameter derived from the volume V signal such as dV/dt MAX.

FIG. 6 depicts the steps of determining the RF parameter in step S414 of FIG. 4. During these pressure measurements, the intrinsic heart rate is determined, and the heart is paced at a pacing rate just above the intrinsic heart rate in order to rigorously control for rate (force-interval) and Frank-Starling filling time (length-tension) effects. It should be noted that it is desirable to avoid pacing, in part or completely if a normal heart rate and stable rhythm exists to help reduce any extra arrhythmia risk associated with the pacing. It should also be noted that pacing can be altogether eliminated by relying upon intrinsic premature beats or extrasystoles. An IMD that is programmed to continuously monitor the electrogram and pressure signals can wait until the heart rate is stable and regular to make the RF parameter assessment and can afford to discard RF parameter assessments that are made over a series of heart beats where the heart rate or rhythm deteriorates or the extrasystole is not timed well. However, since it is the more complex process, FIG. 6 depicts the RF parameter measurement taking place during fixed rate pacing.

When the RF parameter measurement process is entered, it is necessary to determine the intrinsic EI in steps S604 and S606. In step S608, a pacing EI is calculated that is sufficiently shorter than the intrinsic EI to overdrive pace the heart chamber, and an ESI is calculated as a fraction of the pacing EI or is determined during the initial baseline programming and measuring steps S402 and S404. The ESI is generally chosen to be as short as possible but to exceed the refractory period of the heart chamber that takes place as the cardiac cells repolarize following a preceding pacing pulse to ensure that the heart will respond and depolarize. Alternatively, the T-wave repolarization waveform of the EGM can be sensed, and the ESI determined as a function of the Q-T interval for this or any of the other sensor signal parameters that depend on an ESI.

Then, the IMD enters a fixed rate pacing mode in step S610 successively delivering "M" pacing pulses at the time-out of the EI to stabilize the heart rate and mechanical pumping function of the heart. The pressure sensor power supply and signal processor 162 is subsequently enabled to measure the heart chamber blood pressure and provide the P and dP/dt signals to control and timing system 102. A reference dP/dt MAX value is measured during one of the fixed rate pacing cycles or several dP/dt MAX values are measured and averaged to provide the reference dP/dt MAX value in step S612. If a sense event occurs during the fixed rate pacing cycles, the RF parameter measurement is aborted.

For simplicity, these steps S602–S612 can be the same as steps S502–S532 of FIGS. 5A and 5B, where M=8, for example. In addition, the determination of the MR parameter and the RF parameter can be made simultaneously.

An ES pulse or pulse train is then delivered in steps S614 through S618 in the next paced heart cycle. Alternatively, a series of such ES pulses or pulse trains can be delivered in a like series of paced heart cycles by repeating steps S614–S618 a number of times, e.g., three times. In either case, the pressure sensor power supply and signal processor 162 is enabled to measure the heart chamber blood pressure and provide the P and dP/dt signals to control and timing system 102. The RF dP/dt MAX values are then determined and temporarily stored over "K" succeeding heart cycles in steps S620–S634 in order to derive the RF time constant in step S636. The RF parameter measurement is terminated if an extrasystole occurs and is sensed in step S626.

Alternatively, when fixed rate pacing is not employed, sense events are detected and mark the end of a preceding heart cycle and the beginning of the next heart cycle. The intrinsic heart rate and rhythm are examined to ensure that they are relatively stable, and the RF measurement is aborted if the intrinsic heart rate and rhythm alters significantly enough to distort the measurement.

An EI count is incremented in step S632, and the measurement of the RF dP/dt MAX values over the remaining heart cycles is repeated in steps S620–S630 until "K" heart cycles are counted. The RF time constant is determined in step S636 and stored with the date and time stamp and any other useful related data after the EI count reaches "$K_{MAX}$", as determined in step S634.

It should be noted that at least the initial dP/dt MAX values following the delivery of the ES stimulation should be larger than the dP/dt MAX (SS) determined in step S612. The determination of the RF time constant in step S636 may be aborted if the dP/dt MAX (SS) determined in step S612 is greater than at least the first post ES stimulation P/dt MAX value.

The determination of RF is made from the decay of the K dP/dt MAX amplitudes from dP/dt $MAX_{k=1}$. The following explanation is made with respect to FIGS. 10–12.

Notation:

time, t cardiac cycle, k

R—R interval, $RR_k$

Baseline R—R interval, $RR_O$

Premature (extrasystolic) R—R interval, ESI

RV dP/dt MAX, dP/dt$_k$

Baseline RV dP/dt MAX. dP/dt$_0$

Figure 10:
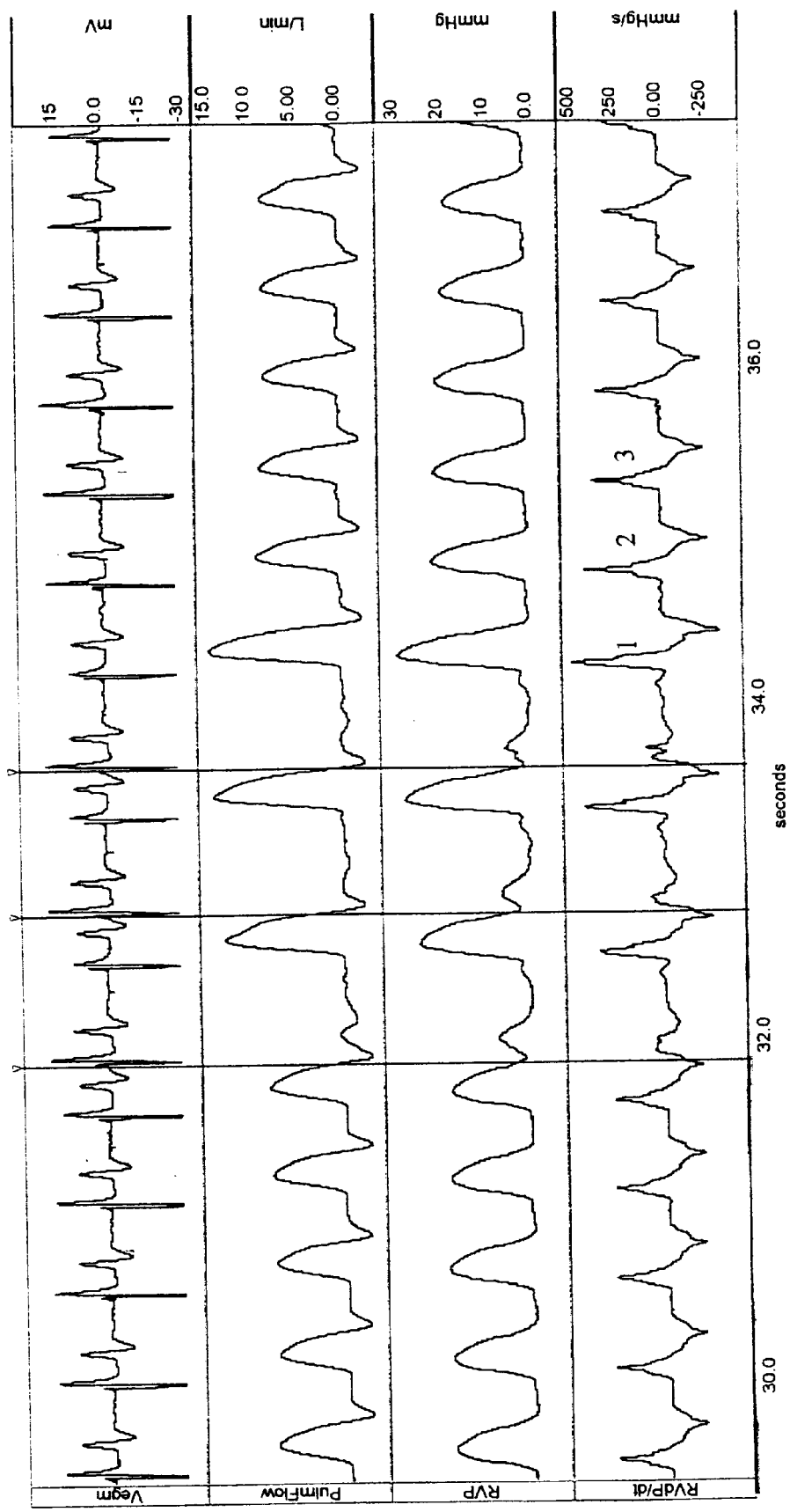
FIG. 10 depicts signals taken during an animal study illustrating the increased contractile performance during subsequent heart beats following delivery of extrasystolic stimulation.
Figure 11:
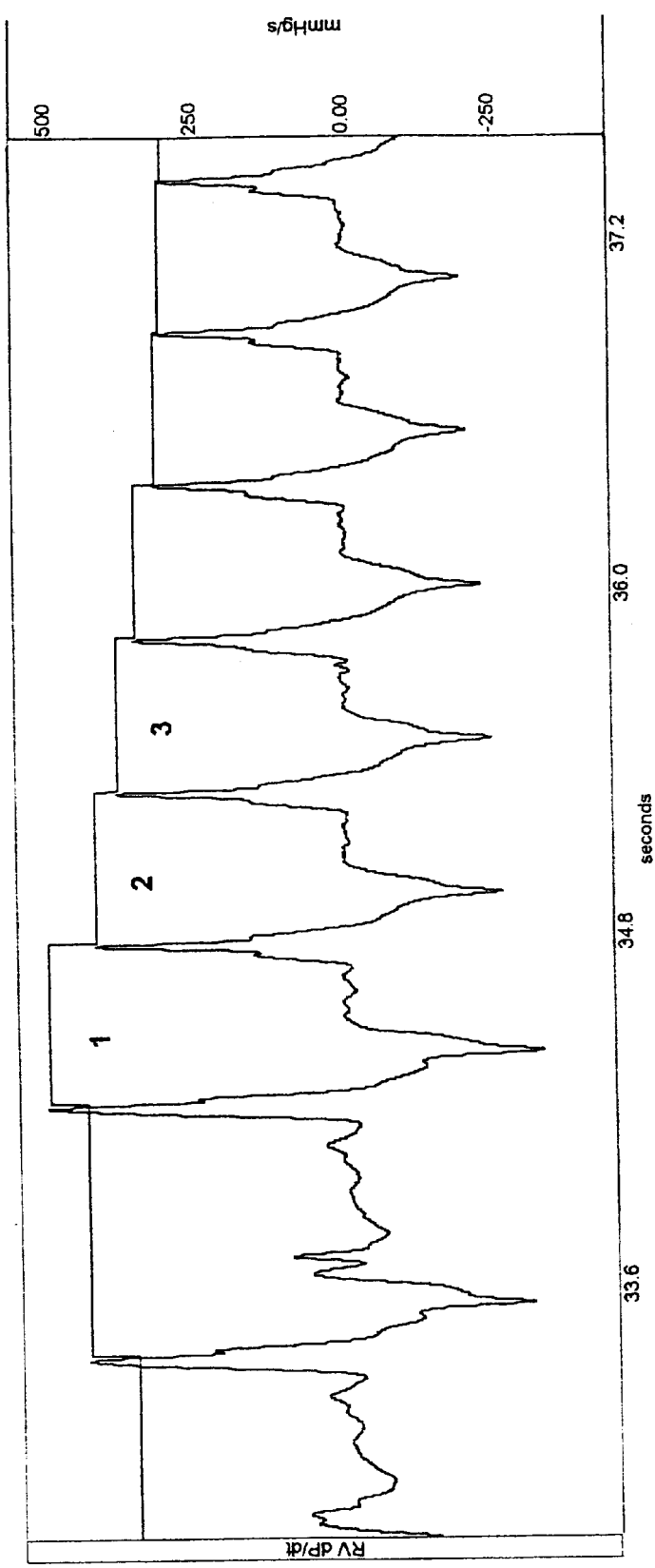
FIG. 11 is an expansion of part of FIG. 10 depicting the elevation RV dP/dt signals due to the delivered extrasystolic stimulation and the decay of RV dP/dt signals over cardiac cycles following termination of the extrasystolic stimulation.
Figure 12:
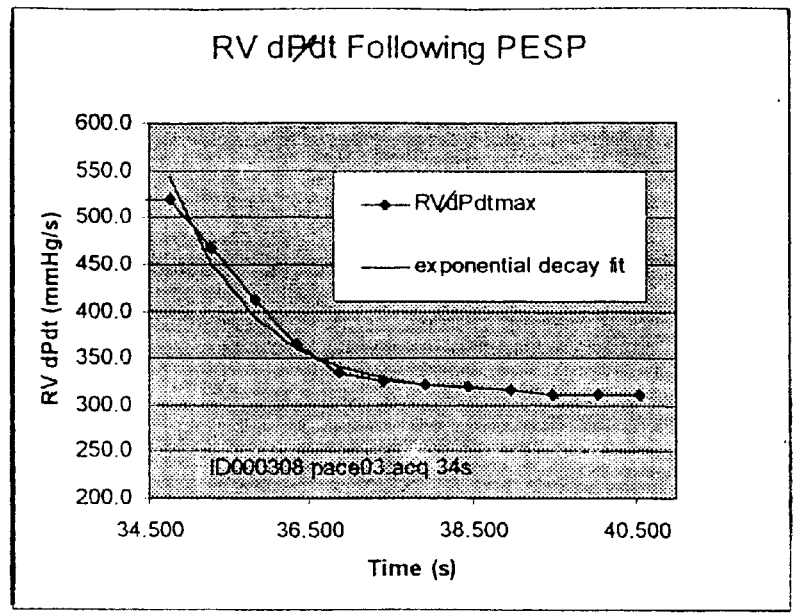
FIG. 12 is a graphical depiction of the exponential decay of dP/dt MAX over cardiac cycles following termination of the extrasystolic stimulation depicted in FIG. 10.

Steps:
  Wait for (or pace) a series of suitable R—R intervals
    Note RR$_0$ and corresponding dP/dt$_0$
    Confirm RR stable and in a normal range
  Pace the atrium or ventricle at the time-out of the ESI to produce one or more premature ventricular beats (extrasystoles) not long after the end of the preceding cycle's refractory period or T wave.
    Confirm ESI<RR$_0$
  Return to the (paced) R—R intervals of the first step for subsequent beats k=1, K$_{max}$
    Record RR$_k$ and dP/dt$_k$
    If RR$_k$ are approximately equal to RR$_0$ and if dP/dt$_1$>dP/dt$_2$>dP/dt$_0$ Compute RF from the slope of the dP/dt$_{k+1}$ versus dP/dt$_k$ data series where k=1, K$_{max}$ FIGS. 10 and 11 illustrate signals from an animal study including the measured ventricular EGM (Vegm), pulmonary flow, right ventricular blood pressure (RVP), and RV dP/dt. The heart rate is regular and stable in the heart cycles preceding the delivery of three paced extrasystoles marked by the three vertical lines. Three pacing energy ES pulses are delivered in the right ventricle after an ESI timed from the detected R-wave and just following the end of the QT interval, resulting in increased contractile performance of the RV which subsequently decays over K heart cycles starting at k=1. FIG. 12 also graphically illustrates the exponential decay of RV dP/dt MAX over the K cardiac cycles following the applied three ES pulses. The RF parameter is derived from the decay in the dP/dt MAX values over cardiac cycles k=1, 2, 3, . . . K counted from the last applied ES pulse.

The dP/dt MAX values and their cardiac cycle indices k=1, 2, 3, . . . K, are stored in IMD memory for determination of the RF parameter as described above.

Figure 13:
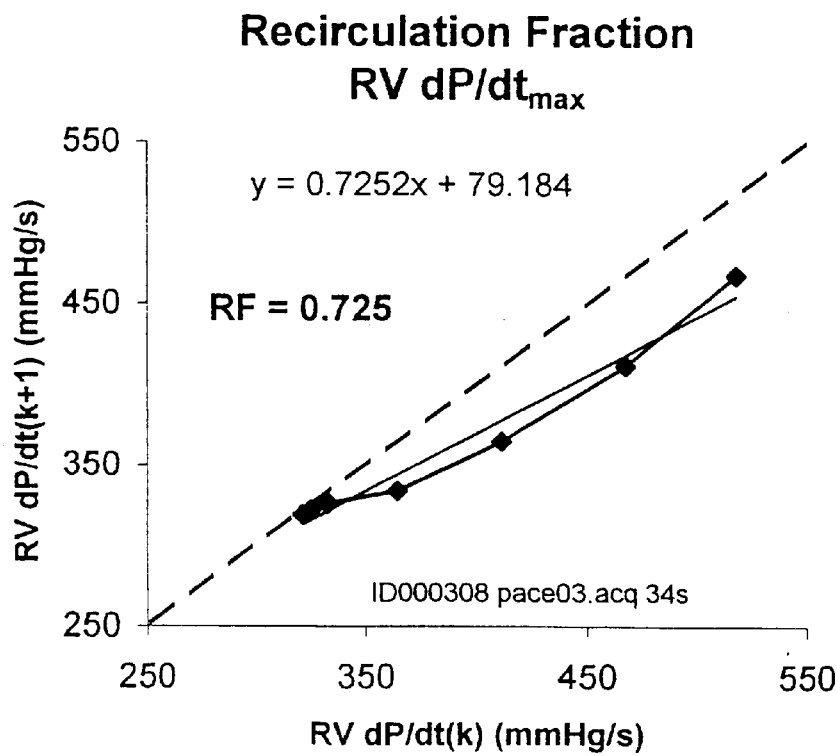
FIG. 13 is a graphical depiction of the signal processing of the exponential decay of dP/dt MAX over the cardiac cycles following termination of the extrasystolic stimulation depicted in FIG. 10 to yield the RF parameter.

FIG. 13 graphically illustrates the determination of the RF parameter from the decay of the dP/dt MAX values over cardiac cycles k=1, 2, 3, . . . K. The slope of the line determined by linear regression is RF=0.725. Roughly 75% of the potentiation manifest on a previous beat is evident on the current beat. Steady state or reference RV dP/dt MAX is approximately 320 mm Hg/s in this example from an anesthetized normal dog.

If desired, it is possible to convert from RF to beat or time constant where:
  Beat constant=–[In(RF)]$^{-1}$, (the number of cycles needed for potentiated dP/dt to decay to 1/e).
  Time constant=–RR$_0$/In(RF), (the time needed for potentiated dP/dt MAX to decay to 1/e).

For this example, the beat constant is 3.1 beats and time constant is 1.6 seconds.

Collection of Tau Parameter Data:

The ventricular relaxation time constant or tau ($\tau$) parameter is believed to be a useful indicator of the state of heart failure and can provide an indication of the state of progression or regression of the heart failure through the comparison of tau parameter data collected over time. The primary information necessary to compute a time constant of relaxation or tau is the drop in ventricular pressure at the end of systole and in the first part of diastole. In the preferred embodiment, an EGM signal, e.g., the R-wave, is used to define cardiac cycle boundaries and to measure R—R intervals, and a continuous pressure P signal, e.g., RVP, is processed to reveal tau for each cardiac cycle where it is measured. Alternatively, a relaxation time constant may also be determined from an analogous computation with the volume signal.

The basic computational algorithm is described below in reference to FIGS. 4 and 8 employing the notation:
  time, t
  cardiac heart cycle, k
  R—R interval, RR$_k$
  Baseline R—R interval, RR$_0$
  Ventricular pressure, P(t)
  Maximum ventricular pressure, P$_{max}$
  Time of occurrence of P$_{max}$, T$_{Pmax}$
  Relaxation time constant, tau$_k$
  Time of occurrence of dP/dt$_{min}$, T$_{dPdtmin}$ The tau parameter is periodically measured from time to time to collect a data set stored in IMD memory along with time and date stamp and other patient data of interest to determine if the tau parameter is relatively unchanged or has changed from an earlier uplink telemetered set of such data. It is desirable that the RR$_k$ interval of each measured tau parameter of the stored data set is comparable so that the tau parameter is not distorted by heart rate variability. The tau parameter measurement can be made in a single heart cycle "k" where the current RR$_k$ is not significantly different than a baseline interval, RR$_0$, determined in one or more preceding heart cycles k$_1$, k$_2$, et seq. In this case, the determined tau parameter and the intrinsic RR$_0$ and RR$_k$ may all be date and time stamped and stored in IMD memory with other relevant patient data, so the stored tau parameter values can be correlated with the RR$_0$ and RR$_k$.

However, the heart can be paced at a rate just above the intrinsic EI to provide a paced RR$_k$ in order to rigorously control for rate (force-interval) and Frank-Starling filling time (length-tension) effects during this measurement. Or, the heart could be paced at a programmed, relatively high, pacing rate to provide a series of paced baseline RR$_0$ followed by a paced RR$_k$ unless the intrinsic heart rate exceeds the programmed paced heart rate. When all conditions are met the determined tau parameter and the paced RR$_0$ and RR$_k$ may all be date and time stamped and stored in IMD memory with other relevant patient data, so the stored tau parameter values can be correlated with the RR$_0$ and RR$_k$.

Figure 8:
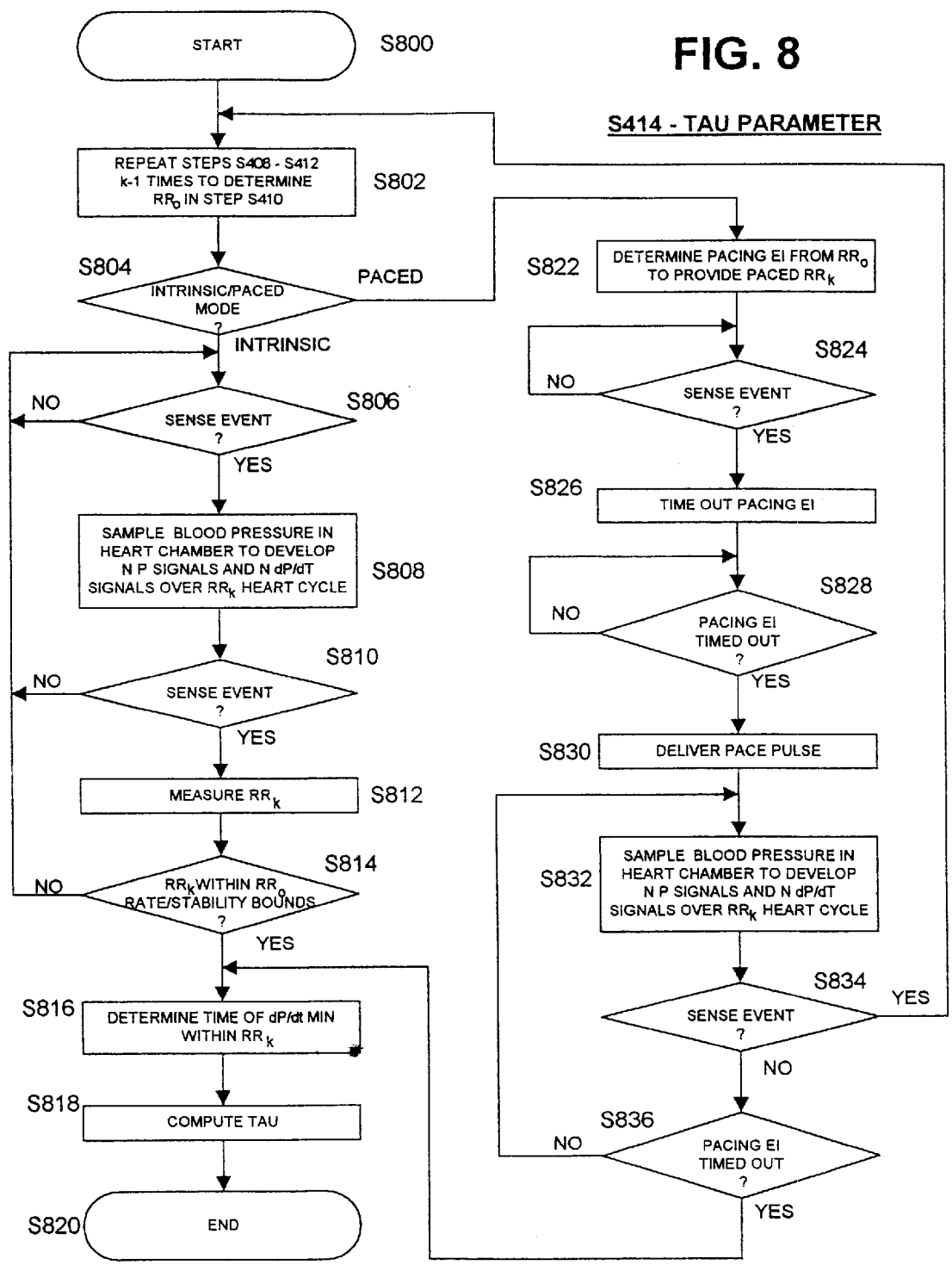
FIG. 8 is a flow chart expanding upon steps of FIG. 4 and depicting the steps of deriving the relaxation time constant s parameter indicative of the heart failure state from certain signals output by a monitoring and pacing channel of FIG. 3.

FIG. 8 illustrates the blood pressure measurements taking place during an intrinsic RR$_k$ that is within RR$_0$ bounds in steps S806–S814 or a paced RR$_k$ that is not interrupted by a early or extrasystolic sense event in steps S822–S836. If the conditions are satisfied, then the determination of tau takes place in steps S816 and S818. At the outset, steps S408 through S410 of FIG. 4 must be satisfied for k$_{-1}$, k$_{-2}$, etc., heart cycles to determine a baseline intrinsic RR$_0$. in Step S802, and the determination is made in step S804 whether the tau is to be determined during an intrinsic or paced RR$_k$. This determination may be based on a programmed preference that is always followed or the IMD may be programmed to preferentially follow the steps S806–S814 but to revert to steps S822–S836 if step S814 is not satisfied one or more times Assuming that the tau parameter is measured during an intrinsic RR$_k$ as determined in step S804, the RR$_k$ interval is started on the next sense event detected in step S806 would typically be the RV R-wave, but the onset of RV dP/dt and a threshold criterion could be employed instead. Upon detection of a sense event in step S806, the pressure sensor power supply and signal processor 162 is enabled to measure the heart chamber blood pressure and provide blood pressure signals to control and timing system 102. The blood pressure in the heart chamber, e.g., the RV, is sampled in step S808 while the intrinsic $RR_k$ times out between the beginning and ending sense event to derive the "N" sampled and digitized pressure values, e.g., N RVP and N RV dP/dt digitized samples. The intrinsic $RR_k$ is measured in step S812 after the ending sense event is detected in step S810, and the measured intrinsic $RR_k$ is compared to the reference $RR_0$ in step S814 to determine if the difference is within defined bounds for rate and rate stability. The N RVP and N RV dP/dt digitized samples are discarded if the intrinsic heart rate and rhythm of the current intrinsic $RR_k$ varies significantly enough to make the tau measurement of steps S816 and S818 atypical.

Steps S822–S836 are followed if the paced mode is determined in step S804, and if pacing rate that is employed would overdrive the intrinsic heart rate reflected by the intrinsic baseline $RR_0$ determined in step S802. In this illustrated embodiment, the paced $RR_k$ is determined from the intrinsic baseline $RR_0$ in step S822 as a pacing EI. The pacing EI is timed out after the next sense event in steps S826 and S828, and a first pacing pulse is delivered in step S830 commencing the paced $RR_k$. As noted above, a paced baseline $RR_0$ could first be developed over a number of paced heart cycles using the determined pacing EI. In addition, the pacing EI could be programmed to overdrive the patient's typical intrinsic heart rate.

The pressure sensor power supply and signal processor 162 is enabled in step S832 to measure the heart chamber blood pressure and provide blood pressure signals to control and timing system 102. The blood pressure in the heart chamber, e.g., the RV, is sampled in step S832 while the intrinsic $RR_k$ times out from the pacing pulse to derive the "N" sampled and digitized pressure values, e.g., N RVP and N RV dP/dt digitized samples.

The RVP and RV dP/dt digitized samples derived in step S832 are discarded if a sense event occurs in step S834 before the pacing EI times out as determined in step S836. In this case, the tau measurement would be aborted or restarted back at step S802.

If the intrinsic or paced $RR_k$ are acceptable, then the N RVP and N RV dP/dt digitized samples derived in step S808 or S832 are subjected to one of the following algorithms to determine the sample time that dP/dt MIN sample was derived in step S816. this is accomplished by looking for the time corresponding to a minimum of the dP/dt signal or for the pressure to have declined to a specific fraction of its maximum for this cardiac cycle. Denote this time, $a_k$, which is constrained $a > T_{P\ max}$ and calculate it by:

$$\alpha_k = arg\ min\{dP/dt(t)\}, or$$

$$\alpha_k = min\{t | P_{max} - P(t) < 0.8 P_{max}\}.$$

Then tau, $\tau_k$, is computed in step S818 from a suitably low pass filtered version of P and dP/dt by:

$$\tau_k = avg\left\{-\frac{P(t)}{dP/dt(t)}\right\}$$

for $\alpha_k < t < \alpha_k + 40$ ms, or $$\tau_k = min\{t | P(t + \alpha_k) < exp(-1) 0.8\ P_{max}\}\ respectively.$$

This estimate of tau is used in subsequent data logging, diagnostic, or therapeutic steps only if it is in a suitable range. The calculated tau value is date and time stamped and stored in IMD memory with other related patient data of interest.

Figure 15:
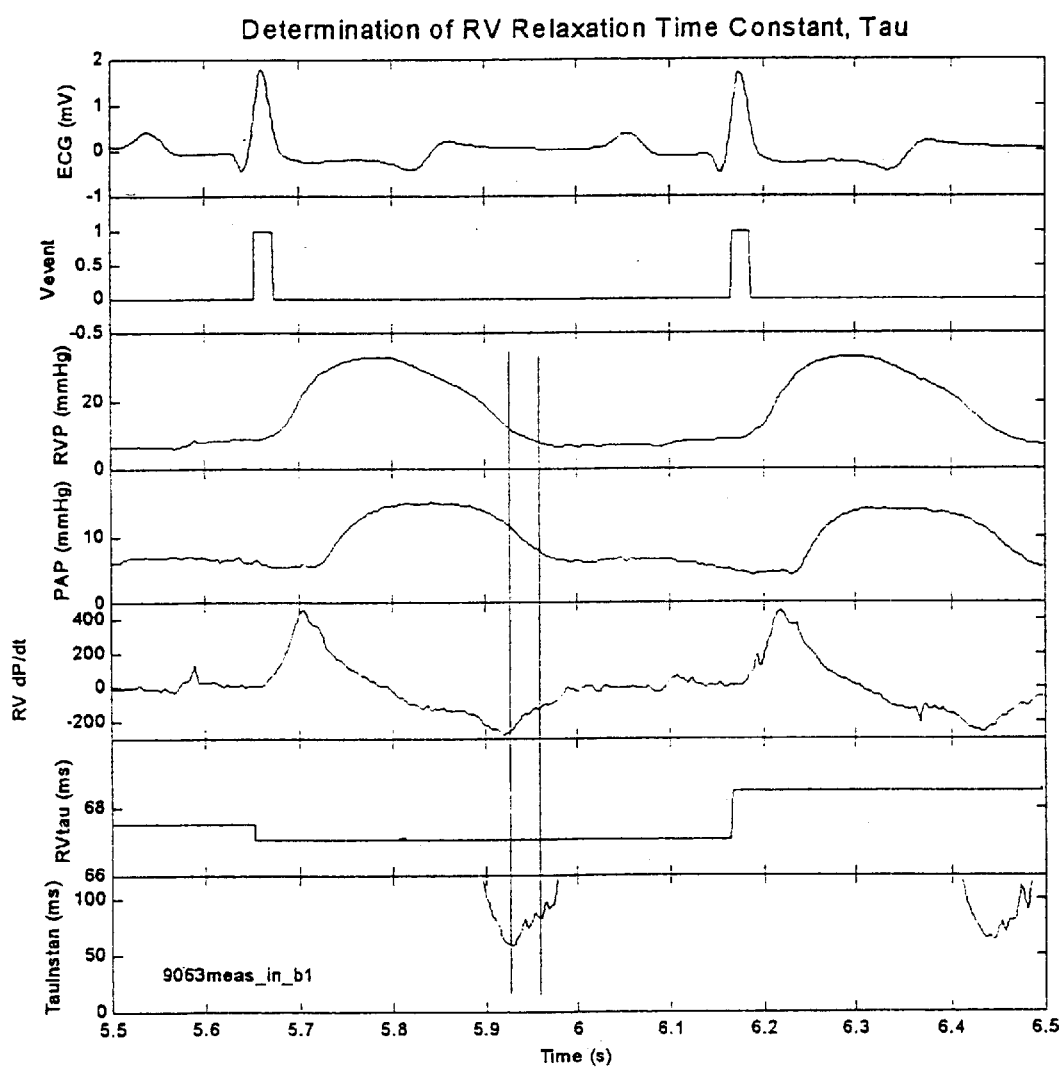
FIG. 15 depicts signals taken during an animal study illustrating the determination of relaxation time constant tau in a time window of an RV pressure signal waveform related to dP/dt MIN.
Figure 17:
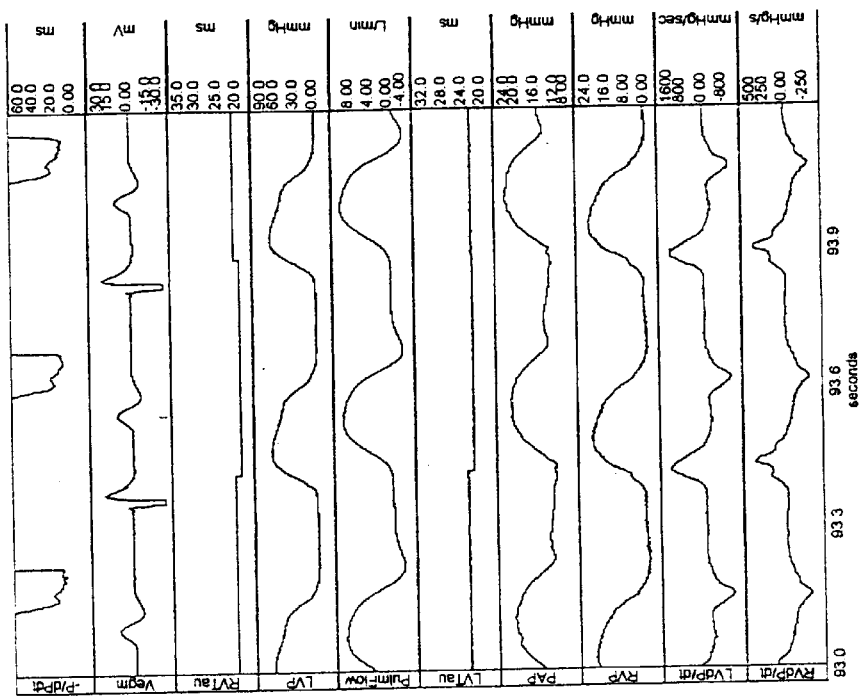
FIG. 17 depicts signals taken during the animal study of FIG. 16 illustrating the relationship of RV and LV tau determined in a time window of FIG. 15 in the animal heart following drug treatment to enhance contractility and relaxation.
Figure 16:
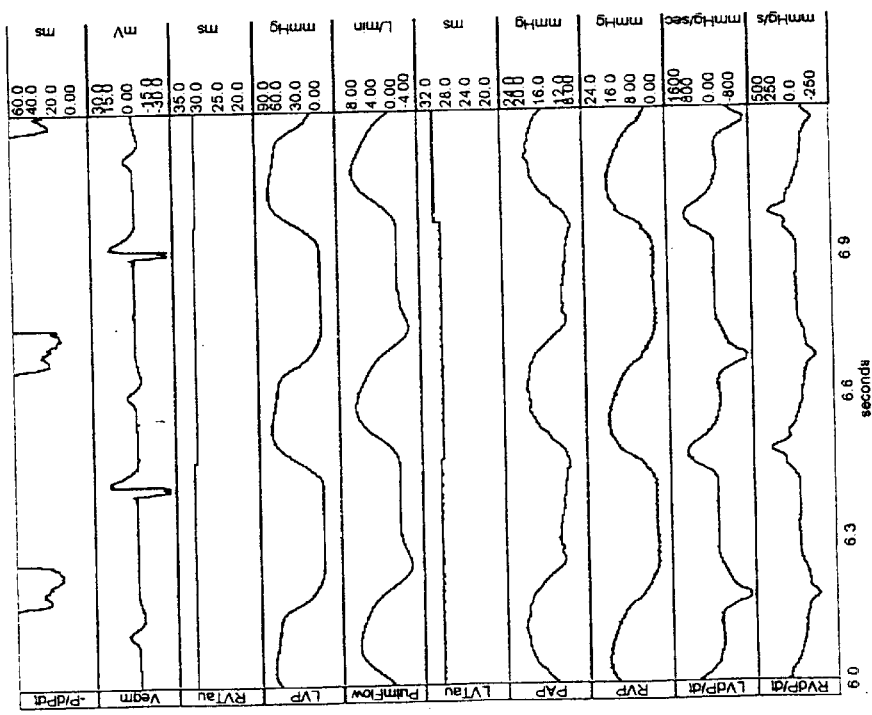
FIG. 16 depicts signals taken during an animal study illustrating the relationship of RV and LV tau determined in a time window of FIG. 15 in a normal animal heart.

Computation of relaxation time constant tau from an RV pressure signal is also illustrated in the waveforms of FIGS. 15–17. FIG. 15 illustrates the computation of the relaxation time constant tau from the RV pressure signals during an animal study. The exponential decay portion of RVP begins from the time of RV dP/dt MIN at about 5.92 seconds. In this example derived from the instantaneous ratio of P to dP/dt (bottom panel), RV tau is computed to be about 68 ms.

FIGS. 16 and 17 Illustrate the concordance of RV tau and LV tau during an animal study wherein both the RV and LV were instrumented to derive LV pressure (LVP), RV pressure (RVP), LV dP/dt and RV dP/dt. FIG. 16 illustrates baseline conditions, and FIG. 17 illustrates conditions after about 90 seconds intravenous infusion of isoproterenol 0.02 ug/kg/min. Contractility, as evidenced by RV and LV dP/dt in FIG. 17, is enhanced by isoproterenol (LV dP/dt max increased from 1200 to 1440 mm Hg/s). Relaxation is also significantly shortened as seen in both RV tau and LV tau, falling from 32 ms and 31 ms in FIG. 16 to 21 ms and 23 ms respectively, in FIG. 17. But, in both cases, it can be seen that the RV tau closely tracks the LV tau, and that it is feasible to employ RVP and RVP dP/dt to derive an RV tau that is representative of the LV tau, thereby making it safer and simpler to implant the pressure sensor.

It should also be noted that the time constant of ventricular contraction can be determined using an analogous procedure. For example, over a time window immediately preceding dP/dt MAX, the ratio of P to dP/dt can be averaged to yield the time constant of exponential growth of pressure in the isovolumic period. This is an index of systolic function.

Collection of End Systolic Elastance Parameter Data:

The end systolic elastance $E_{ES}$ parameter is believed to be a useful indicator of the state of heart failure and can provide an indication of the state of progression or regression of the heart failure through the comparison of $E_{ES}$ parameter data collected over time. The end systolic elastance $E_{ES}$ parameter comprises a slope determined from a collection or "cloud" of "n" data points of end systolic $P_{ES}$ measurements plotted against the simultaneously determined end systolic heart chamber volume $V_{ES}$ measurements.

Figure 7:
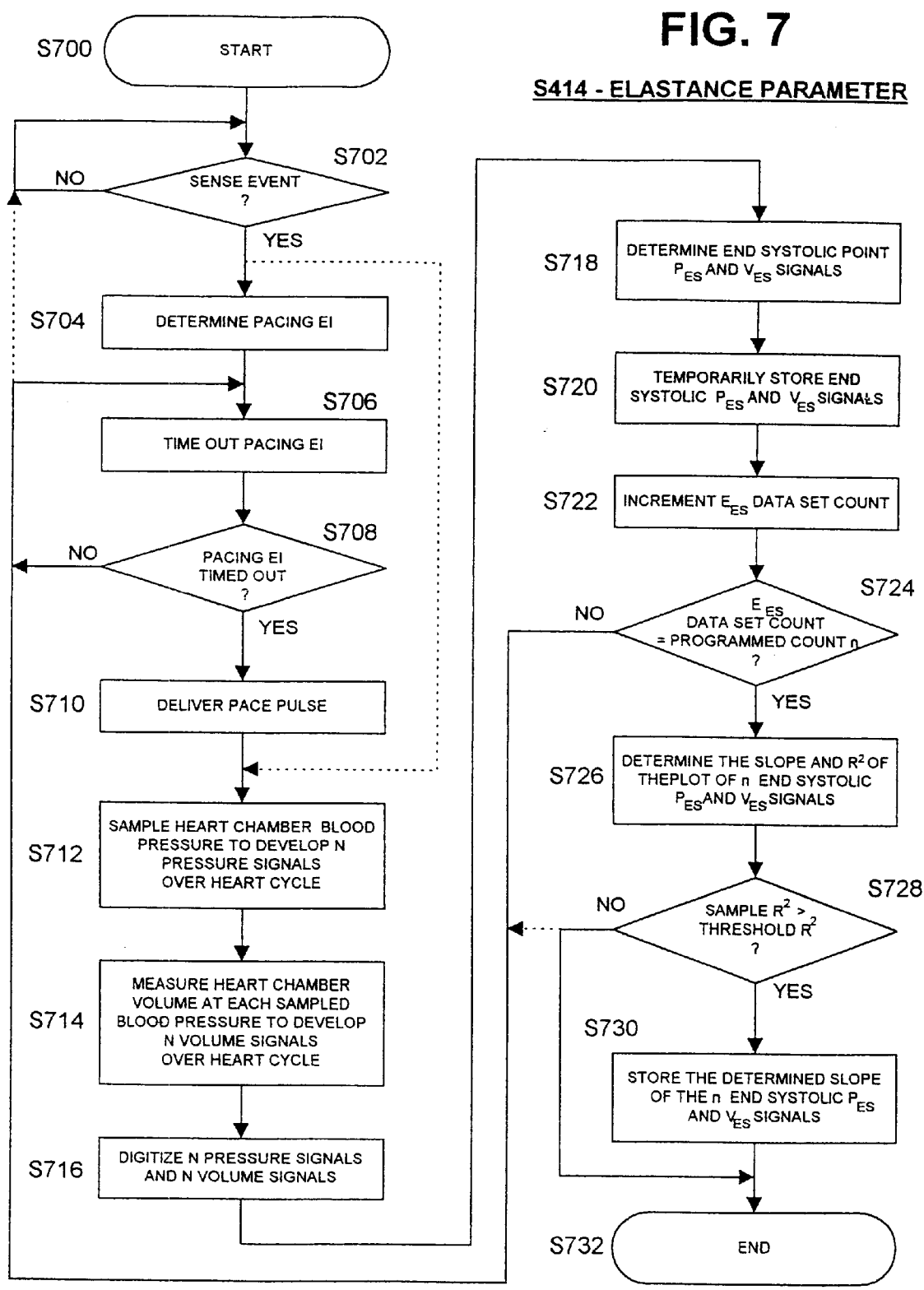
FIG. 7 is a flow chart expanding upon steps of FIG. 4 and depicting the steps of deriving the end systolic elastance $E_{ES}$ parameter indicative of the heart failure state from certain signals output by a monitoring and pacing channel of FIG. 3.

FIG. 7 depicts the steps of determining the $E_{ES}$ parameter in step S414 of FIG. 4. When the $E_{ES}$ parameter measurement is started, it can be conducted during "n" successive paced heart cycles as illustrated in steps S704–S706 or during intrinsic heart cycles as illustrated by the broken lines. In the latter case, it may be advisable to make a determination that the heart rate and rhythm remain within prescribed ranges between steps S702 and S712. In the former case, the pacing EI is calculated that is sufficiently shorter than the intrinsic EI to overdrive pace the heart chamber in step S704, and fixed rate pacing is carried out in steps S704–S708 at least for "n" programmed pacing cycles.

In either case, the pressure sensor power supply and signal processor 162 is enabled in step S712 to measure the heart chamber blood pressure and provide "N" sampled P and dP/dt signals over the heart cycle. At the same time, the impedance power supply and signal processor 180 is enabled in step S714 to develop "N" volume V signals over the heart cycle. The "N" sampled P and dP/dt and volume V signals are digitized in step S716 and applied to control and timing system 102.

The end systolic point $P_{ES}$ and $V_{ES}$ is determined in step S718 and stored in IMD memory in step S720. The determination of the end systolic $P_{ES}$ and $V_{ES}$ samples at the end systolic point in the heart cycle is made by first determining dP/dt MIN sample and selecting a P sample and V sample at a short time, e.g., 20 ms, prior to the dP/dt MIN sample. In this way, "n" sets of $[P_{ES}, V_{ES}]$ data points are accumulated for determination of $E_{ES}$ and derivation of a correlation coefficient R and squared correlation coefficient $R^2$ in step S726.

The $E_{ES}$ data set count is then incremented in step S722, and the incremented count is compared to a programmed data set count "n" in step S724. The process of determining the n end systolic point $P_{ES}$ and $V_{ES}$ values is commenced again for the next intrinsic EI at step S702 or the next paced EI at step S704, and the process is repeated until the programmed data set count "n" is reached.

It should also be noted that the event trigger criteria of step S406 can be programmed in step S402 to be "all times" that step S412 is met or fixed rate pacing is provided in steps S704–S708. In this case, "n" sets of $[P_{ES}, V_{ES}]$ data points are continuously accumulated on a FIFO basis for determination of $E_{ES}$ and derivation of a correlation coefficient R and squared correlation coefficient $R^2$ in step S726. In this variation, steps S722 and S724 are always satisfied when the first "n" sets of $[P_{ES}, V_{ES}]$ data points are accumulated.

Figure 19:
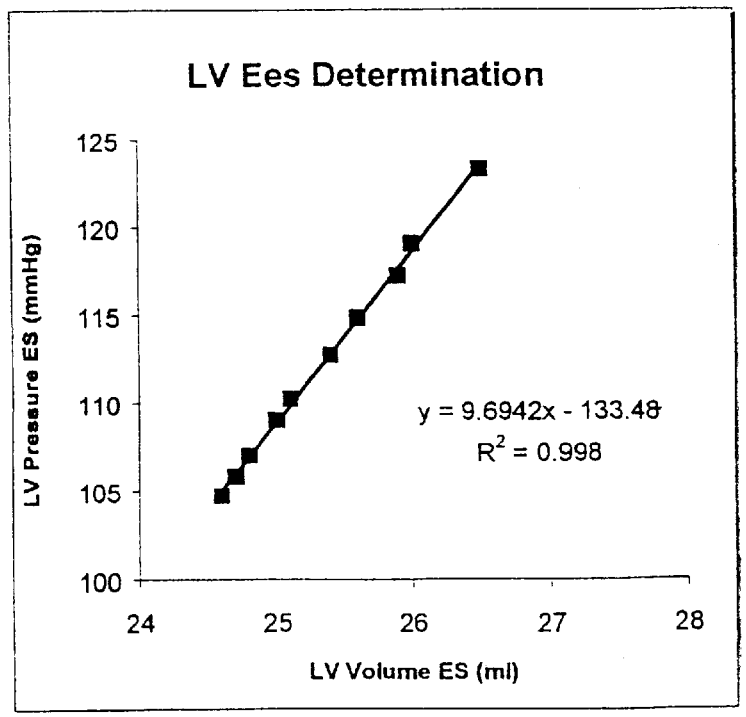
FIG. 19 is a graphical depiction of a linear regression of the end systolic PV points of FIG. 18 to derive the slope of the LV $E_{ES}$.
Figure 21:
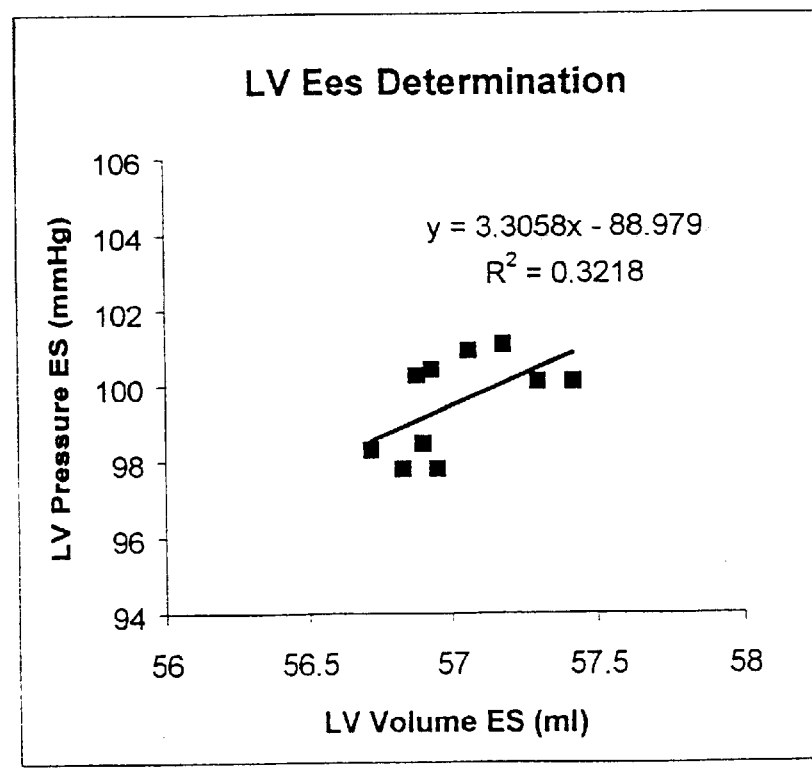
FIG. 21 is a graphical depiction of a linear regression of the end systolic PV points of FIG. 20 wherein the determination of slope of the LV $E_{ES}$ is not reliable.

Then, in either case, in step S726, a linear regression of the "n" sets of $[P_{ES}, V_{ES}]$ data points is conducted using standard linear regression techniques to derive the slope of the sampled data set, $E_{ES}$, a correlation coefficient R and the squared correlation coefficient $R^2$ as depicted in FIGS. 19 and 21 as described further below.

In step S728, the squared correlation coefficient $R^2$ of the "n" sets of $[P_{ES}, V_{ES}]$ data points data set (the sample squared correlation coefficient $R^2$) is compared to a threshold squared correlation coefficient $R^2$ (e.g. 08–0.9) that is initially programmed in step S402.

The slope of the sampled data set of "n" end systolic $[P_{ES}: V_{ES}]$ data points determined in step S726 is saved as the $E_{ES}$ in step S730 if the sample squared correlation coefficient $R^2$ exceeds the threshold squared correlation coefficient $R^2$ value as determined in step S728. If the threshold condition is not met, then a slope of the sampled set of "n" end systolic $[P_{ES}, V_{ES}]$ values cannot be meaningfully determined. The accumulated data set is either discarded and the $E_{ES}$ parameter measurement aborted as shown in FIG. 7 or the data set is updated on a FIFO basis by starting again at either step S702 or step S706. The accumulated data set and/or slope $E_{ES}$ is then saved with other associated data in IMD memory in step S730 if the slope can be determined from the clustered plotted intersecting data points of "n" end systolic $[P_{ES}, V_{ES}]$ values.

Figure 18:
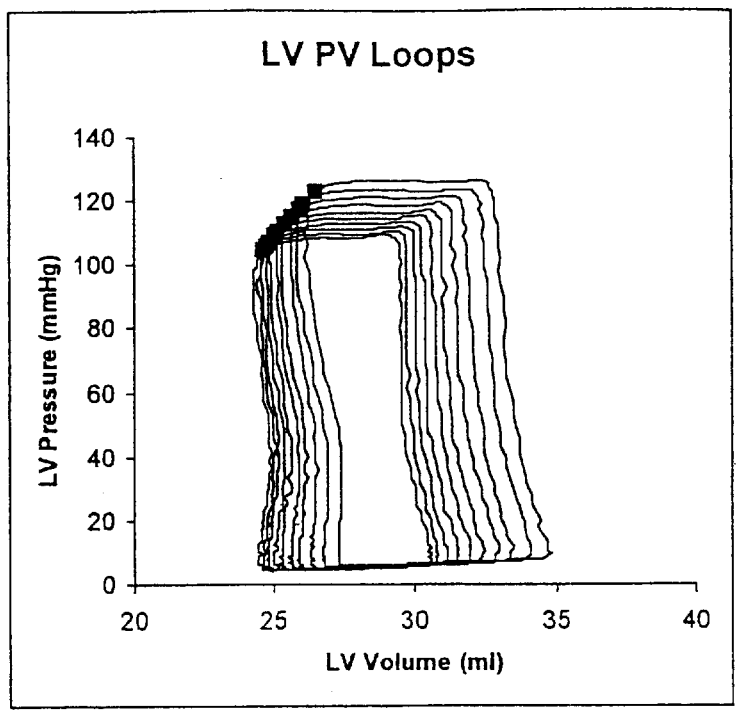
FIG. 18 is a graphical depiction of measured left ventricular PV loops during a modification of preload with end systolic PV points shown at the upper left.

FIG. 18 is a plot of ten consecutive PV loops during a modification of preload (vena caval partial occlusion) with end systolic PV points shown at the upper left of FIG. 18. When a linear regression is performed using these ten end systolic PV points of FIG. 18, a straight line is formed as shown in FIG. 19. The fit of the line shown in FIG. 19 to the points is very good with correlation $R^2=0.998$. An end systolic elastance $E_{ES}$ of 9.69 is evidenced by the slope of the line. It is expected that the slope will change in a manner that signifies the progression or remission of heart failure in a patient's heart.

Figure 20:
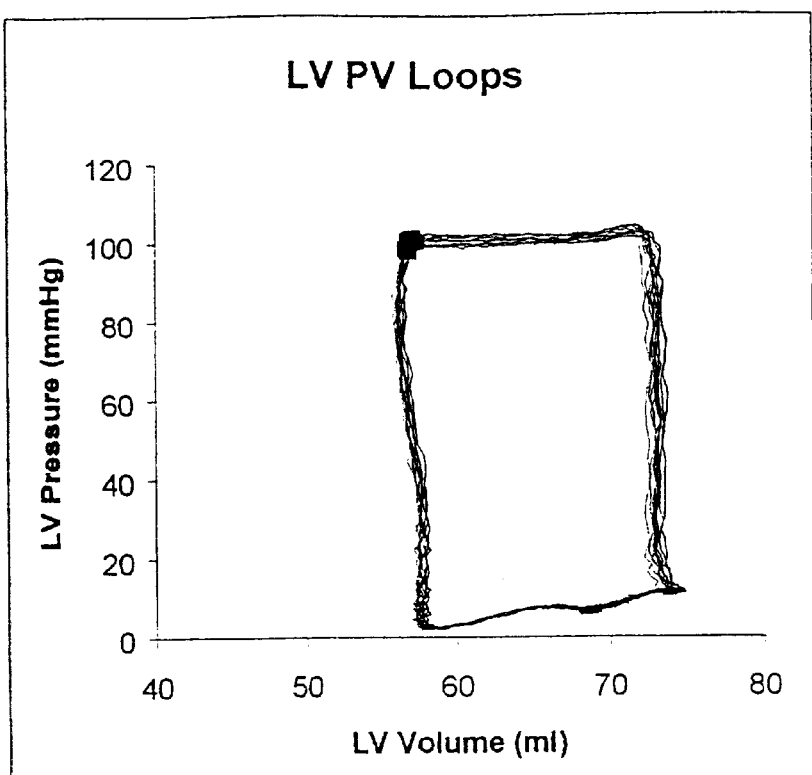
FIG. 20 is a graphical depiction of measured left ventricular PV loops during normal heart function with end systolic PV points shown at the upper left.

By contrast, FIG. 20 is a plot of ten consecutive PV loops at a baseline condition of a relatively normal heart evidencing little physiologic change in the measured P and V. As a result, the ten end systolic PV points are on top of each other in the upper left corner of FIG. 20. When a linear regression is performed using these ten end systolic PV points in FIG. 21, these points do not reliably form a good straight line and thus do not permit an estimation of $E_{ES}$. The correlation of $R^2=0.322$ is sufficient to recognize that the $E_{ES}$ slope of 3.31 is not an accurate reflection of the physiology and would be discarded following the comparison step S726.

The end systolic elastance $E_{ES}$ is computed periodically or continuously in this manner to store a set of such slopes. The stored slopes are retrieved by uplink telemetry to an external programmer and are subjected to linear regression analysis to determine if a more recent slope has changed from an earlier slope in a manner that signifies a deterioration or improvement in CHF. A decrease in $E_{ES}$ implies a decrease in systolic function and loss in contractile strength.

Figure 23:
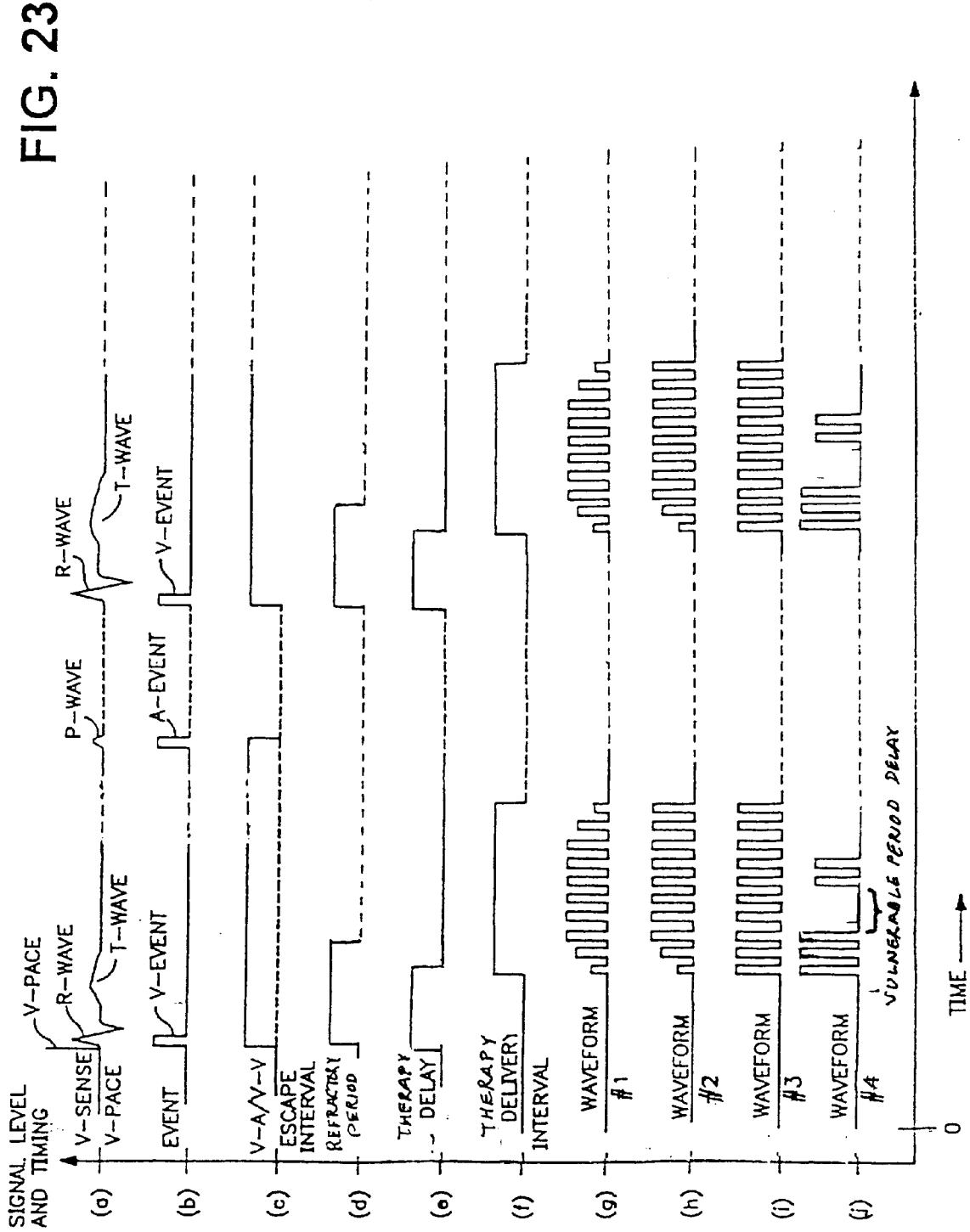
FIG. 23 depicts the delivery of therapeutic PESP stimulation, particularly, pacing energy pulse trains commenced during the refractory period of the heart and continuing for a PESP delivery interval.

Therapy Delivery:

Turning to FIG. 23, the timing diagram illustrates the timing of delivery of stimulation to a heart chamber by the PESP/PACE output pulse generator 150 of FIG. 3 in relation to a timed interval from a sensed or paced event as well as alternative pulse waveforms of the ES stimulation. In accordance with one aspect of the present invention, a therapeutic stimulation delay illustrated in tracing (e) is timed out from a sensed or paced event (e.g., the illustrated V-EVENTs) that is shorter than the refractory period of the heart persisting from the sensed or paced event. A stimulus pulse train is delivered to the atria and/or ventricles in the depicted therapy delivery interval of tracing (f) commencing after time-out of the delay so that at least the initial pulse(s) of the pulse train fall within the end portion of the refractory period. The pulses of the PESP portion of the delivered therapies are intended to be supra-threshold in nature, that is, of sufficient energy to depolarize the heart when they are delivered in the non-refractory period of the heart cycle so that the heart is captured by at least one of the PESP pulses falling outside the refractory period. The initial pulses delivered during the refractory period can also potentiate the heart. For simplicity of illustration, the tracings (f)–(j) are expanded in length, and the depolarization of the heart that they cause is not depicted in tracing (a). The amplitude and number of refractory interval pulses and PESP pulses in each therapy pulse train and the spacing between the pulses may also differ from the illustrated tracings (g)–(j).

The ventricular sense or pace event detected in tracing (b) also triggers the timing out of an escape interval in tracing (c) which may be terminated by the sensing of a subsequent atrial or ventricular event, depending on the operating mode of the system. The first depicted sequence in FIG. 23 shows the full time-out of the escape interval in tracing (c), the refractory period in tracing (d), and the therapy delay and delivery intervals in tracings (e) and (f). The therapy delay and therapy delivery intervals can be derived as a function of an intrinsic V-V or V-A escape interval derived by measuring and averaging intervals between intrinsic ventricular and/or atrial sense events or paced events. The therapy delay can also be determined from a measurement of the QT interval. As illustrated, the therapy delay in tracing (e) delays delivery of the therapy pulse train until the QRS complex ends or about 40–60 ms after the V-EVENT well before the start of the vulnerable period of the heart which occurs near the end of the T-wave. The therapy delivery interval is timed to time-out well before the end of the previously derived V-V or V-A escape interval, but is extended for ease of illustration of the pulse trains in tracings (f)–(j).

The therapy stimulation energy is delivered in the form of a burst of X constant or variable energy stimulation pulses separated by a pulse separation interval between each pulse of the burst. All of the pulses can have the same amplitude and energy as shown in waveform 3 of tracing (j). Or the leading and/or trailing pulses of the pulse train can have ramped amplitudes similar to the waveforms 1 and 2 illustrated in tracings (g) and (h). In tracings (g) and (h), the ramp up leading edge amplitudes of a sub-set of the pulses of the burst are shown increasing from an initial amplitude to a maximum amplitude. In tracing (g), the ramp down trailing edge amplitudes of a further sub-set of the pulses of the burst are shown decreasing from the maximum amplitude to a terminating amplitude.

Alternatively, the initial set of pulses delivered during the refractory period can have a higher pulse amplitude or width as shown by waveform 4 illustrated in tracing (j). The high energy pulses delivered during the refractory period can enhance the PESP effect during subsequent heart cycles. Tracing (j) also illustrates alternative numbers and spacing of the pulses of the pulse train, and it will be understood that this embodiment can also employ the number of pulses and pulse spacing of waveforms 1–3.

In addition, it may be desirable to avoid delivering any therapy pulses in the vulnerable period of the heart near the end of the T-wave, particularly if high energy pulses are delivered during the refractory period. Tracing (j) also illustrates a vulnerable period delay between the high energy pulses delivered during the refractory period and the lower energy PESP pulses to avoid delivering any pulses during the vulnerable period of the heart. It would also be possible to lower the pulse energy of the pulses delivered later in the refractory period.

The therapy delivery capability is preferably implemented into a system that may include conventional pacing therapies and operating modes as well as cardioversion/defibrillation capabilities or as a stand alone system for simply providing pulse therapies to effect potentiation of myocardial cells between sensed PQRST complexes shown in FIG. 23.

Conclusion:

The above-described methods and apparatus are believed to be of particular benefit for patient's suffering heart failure including chronic CHF and its variants as described above. It will understood that the present invention offers the possibility of monitoring and treatment of a wide variety of acute and chronic cardiac dysfunctions arising from:

The above described methods and apparatus are believed to be of particular benefit for patients suffering from heart failure including chronic HF and its variants as described above. It should be understood . . . a wide variety of acute and chronic cardiac mechanical dysfunctions arising from:

Acute and chronic heart failure;

Cardiogenic shock;

Drug overdoses including agents commonly used to treat HF such as beta blockers;

Protracted tachyarrhythmias (e.g. VT, AT/AF) or bradycardia;

Electromechanical dissociation;

Cardiac dysfunction or pulse-less electrical activity associated with resuscitation;

Post cardiac bypass surgery with cardioplegia;

Severe respiratory dysfunction and hypoxia;

Coronary artery ischemia from thrombus or surgical manipulation;

Acute myocardial infarction; and

Any other cardiac dysfunctions and disease processes that will be apparent to the clinician.

Consequently, the expression "heart failure" as used in above and in the following claims shall be understood to embrace the same.

All patents and other publications identified above are incorporated herein by reference.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. In an implantable medical device, a system for monitoring the state of heart failure of the heart of a heart failure patient and delivering a therapy comprising:

pulse generating means for selectively generating and applying a pacing pulse to at least one heart chamber to effect a contraction of the heart chamber commencing a heart cycle and for selectively generating and applying an extrasystolic electrical stimulus to the at least one heart chamber at the time out of an extrasystolic escape interval to induce post-extrasystolic potentiation increasing the strength of contraction of the heart chamber;

electrical signal sense means for sensing the electrical signals of the heart in said at least one heart chamber and providing a sense event signal signifying the contraction of the heart commencing a heart cycle;

heart chamber volume measuring means for measuring the volume of a heart chamber over at least a portion of a heart cycle and providing a chamber volume value;

blood pressure measuring means for measuring blood pressure within a heart chamber over at least a portion of a heart cycle and providing a blood pressure value;

parameter deriving means for selectively enabling operation of said pulse generating means, said electrical signal sense means, said heart chamber volume measuring means, and said blood pressure measuring means for periodically deriving a plurality of heart failure parameters signifying the state of heart failure from selected measured values of chamber volume and blood pressure, the heart failure parameters including:

a tau parameter representing one of a relaxation and contraction time constant of the heart chamber, a mechanical restitution parameter representing the mechanical response of a heart chamber to electrical stimuli applied to the heart chamber prematurely at differing times during a plurality of heart cycles, a recirculation fraction parameter representing the increase in strength of a contraction of the heart chamber in response to an electrical stimuli applied to the heart chamber during a heart cycle and the rate of decay of the increase in strength of successive contractions of the heart chamber over a series of heart cycles; and an elastance parameter representing the slope of plotted sets of end systolic blood pressure versus end systolic chamber volume over a plurality of heart cycles; and therapy delivery means responsive to a determined heart failure parameter for operating said pulse generating means in a therapy delivery mode to increase the strength of contraction of the patient's heart and improve the heart failure state.

2. The implantable medical device of claim 1, wherein said therapy delivery means further comprises:

means for establishing a therapy delay timed from a pacing pulse or sensed event that lapses within the refractory period of the heart but outside the vulnerable period of the heart, a therapy burst pulse number X, and a therapy pulse separation interval between each pulse of a therapy burst of X pulses;

means for timing out the therapy delay and triggering the delivery of one or more burst pacing pulse within the refractory period; and means for timing out the pulse separation interval for each of the remaining burst pacing pulses and triggering the delivery of at least one burst pacing pulse outside of the refractory period to increase the strength of contraction of the patient's heart.

3. The implantable medical device of claim 1, wherein the tau parameter deriving means further comprises means for operating said blood pressure measuring means to make N blood pressure (P) and rate of change (dP/dt) measurements in the heart chamber at a predetermined sample rate over a heart cycle following a natural, intrinsic, or paced depolarization of the heart chamber;

means for determining dP/dt MIN and the time of dP/dt MIN during the heart cycle; and means for deriving the tau parameter at the time of dP/dt MIN as a function of a set of samples of pressure P and dP/dt within a time window measured from the time of dP/dt MIN.

4. The implantable medical device of claim 1, wherein the recirculation fraction parameter deriving means further comprises:

means for operating said pulse generating means to provide fixed rate pacing directly or indirectly to a heart chamber to stabilize the heart rate of the heart chamber at a steady state (SS) over a first predetermined number of paced SS heart cycles;

means for operating said pulse generating means for providing extrasystolic (ES) stimulation to a heart chamber after an extrasystolic interval timed from a pace pulse during each at least one paced ES heart cycle;

means for operating said blood pressure measuring means to make N blood pressure (P) and rate of change (dP/dt) measurements in the heart chamber that is depolarized directly or indirectly by the delivered pacing pulses at a predetermined sample rate over at least a portion of a second predetermined number of paced heart cycles following the last paced ES heart cycle;

means for determining maximum blood pressure rate of change (dP/dt MAX (ES)) during each of the second predetermined number of paced heart cycles following the last paced ES heart cycle, the determined dP/dt MAX (ES) values and the paced heart cycle numbers comprising an RF parameter data set, whereby each determined dP/dt MAX (ES) value of each stored RF parameter data set can be plotted in relation to the paced heart cycle number to exhibit the exponential decay of the dP/dt MAX (ES) values over time that reflects the decay in the PESP effect in the heart chamber after delivery of the ES stimulation.

5. The implantable medical device of claim 4, wherein the recirculation fraction parameter deriving means further comprises:

means for operating said blood pressure measuring means to make N blood pressure (P) and rate of change (dP/dt) measurements in the heart chamber that is depolarized directly or indirectly by the delivered pacing pulse at a predetermined sample rate during at least one SS paced heart cycle;

means for determining a maximum blood pressure rate of change (dP/dt MAX (SS)) during the SS heart cycle; and means for determining that the at least one determined dP/dt MAX (ES) value exceeds the dP/dt MAX (SS) value.

6. The implantable medical device of claim 1, wherein the end systolic elastance parameter deriving means for deriving the slope of plotted sets of end systolic blood pressure versus end systolic chamber volume over a plurality of heart cycles further comprises:

(a) means for operating said blood pressure measuring means and said heart chamber volume measuring means to make N blood pressure (P) measurements and N volume (V) measurements of the heart chamber at a predetermined sample rate over a series of heart cycles following a natural, intrinsic, or paced depolarization of the heart chamber;

(b) means for selecting the end systolic blood pressure ($P_{ES}$) measurements and end systolic volume ($V_{ES}$) measurements at the end systolic point in each heart cycle;

(c) means for establishing a threshold correlation coefficient $R^2$;

(d) means for accumulating n sets of end systolic [$P_{ES}$, $V_{ES}$] data points;

(e) means for performing a linear regression of the "n" sets of [$P_{ES}$, $V_{ES}$] data points to derive the slope of the sampled data set, a sample correlation coefficient R and a sample squared correlation coefficient $R^2$;

(f) means for comparing the sample squared correlation coefficient $R^2$ to the threshold squared correlation coefficient $R^2$; and (g) means for storing the derived slope as the end systolic elastance if the sample squared correlation coefficient $R^2$ exceeds the threshold squared correlation coefficient $R^2$.

7. The implantable medical device of claim 6, wherein the end systolic elastance parameter deriving means further comprises:

means operable if the sample squared correlation coefficient $R^2$ does not exceed the threshold squared correlation coefficient $R^2$ for continuously operating means (a)–(f) to develop the "n" sets of [$P_{ES}$, $V_{ES}$] data points where the oldest set of [$P_{ES}$, $V_{ES}$] data points is replaced by the newest set of [$P_{ES}$, $V_{ES}$] data points on a FIFO basis until the sample squared correlation coefficient $R^2$ exceeds the threshold squared correlation coefficient $R^2$ and for then operating means (g) for storing the derived slope as the end systolic elastance when the sample squared correlation coefficient $R^2$ exceeds the threshold squared correlation coefficient $R^2$.

8. The implantable medical device of claim 1, wherein the mechanical restitution parameter deriving means further comprises:

means for operating said pulse generating means to provide fixed rate pacing directly or indirectly to a heart chamber to stabilize the heart rate of the heart chamber at a steady state (SS) over a first predetermined number of paced SS heart cycles;

means for operating said blood pressure measuring means to make N blood pressure measurements P and dP/dt in the heart chamber that is depolarized directly or indirectly by the delivered pacing pulse at a predetermined sample rate during at least one SS paced heart cycle;

means for determining maximum blood pressure rate of change (dP/dt MAX (SS)) during the SS heart cycle;

means for operating said pulse generating means to provide fixed rate pacing and for providing extrasystolic (ES) stimulation at differing timed extrasystolic intervals timed from a pace pulse during each of a second predetermined number of paced ES heart cycles;

means for operating said blood pressure measuring means to make N blood pressure measurements P and dP/dt in the heart chamber at a predetermined sample rate over at least a portion of each of the second predetermined number of paced ES heart cycles;

means for determining maximum blood pressure rate of change (dP/dt MAX (ES)) during each ES heart cycle; and means for processing each determined dP/dt MAX (ES) with respect to the dP/dt MAX (SS) to derive mechanical restitution data sets from which the time constant of systolic restitution $tc_{mrc}$ is derived.

* * * * *